(12) United States Patent
Herndon et al.

(10) Patent No.: US 6,576,618 B1
(45) Date of Patent: Jun. 10, 2003

(54) METHODS TO ENHANCE WOUND HEALING AND ENHANCED WOUND COVERAGE MATERIAL

(75) Inventors: David N. Herndon; Jose R. Perez-Polo; Robert E. Barrow, all of Galveston, TX (US)

(73) Assignee: Research Development Foundation, Carson City, NV (US)

( * ) Notice: Subject to any disclaimer, the term of this patent is extended or adjusted under 35 U.S.C. 154(b) by 211 days.

(21) Appl. No.: 09/602,183

(22) Filed: Jun. 22, 2000

Related U.S. Application Data
(60) Provisional application No. 60/140,196, filed on Jun. 22, 1999.

(51) Int. Cl.$^7$ ............................................. A61K 91/127
(52) U.S. Cl. ...................... 514/44; 435/320.1; 435/455; 435/458; 424/450
(58) Field of Search ........................... 514/44; 424/450; 435/320.1, 455, 458

(56) References Cited

U.S. PATENT DOCUMENTS

| | | | | |
|---|---|---|---|---|
| 5,064,655 A | * | 11/1991 | Uster ......................... | 424/450 |
| 5,256,644 A | * | 10/1993 | Antoniades et al. .......... | 414/12 |
| 5,651,982 A | * | 7/1997 | Marx ......................... | 424/450 |
| 5,728,546 A | * | 3/1998 | Greene et al. ............. | 435/69.1 |
| 5,741,509 A | * | 4/1998 | Kushner ...................... | 424/443 |
| 5,962,427 A | * | 10/1999 | Goldstein et al. ............ | 514/44 |
| 5,976,878 A | * | 11/1999 | Boyce ........................ | 435/366 |
| 6,120,799 A | * | 9/2000 | McDonald et al. .......... | 424/450 |
| 6,132,765 A | * | 10/2000 | DiCosmo et al. ........... | 424/450 |
| 6,153,631 A | * | 11/2000 | Petrie et al. ................ | 514/367 |

FOREIGN PATENT DOCUMENTS

| | | | |
|---|---|---|---|
| WO | WO 97/07824 | * | 3/1997 |

OTHER PUBLICATIONS

Nakamura, Gene Therapy, vol. 5, 1165–1170, 1995.*
Raz et al. (Vaccines, 94, pp. 71–75, 1994).*
Filion et al. (International J. of Pharmaceutics, 162, pp. 159–170, 1998).*
Verma et al. (Nature, vol. 389, 18, pp. 239–242,. Sep. 1997.*

* cited by examiner

*Primary Examiner*—Dave T. Nguyen
(74) *Attorney, Agent, or Firm*—Benjamin Aaron Adler

(57) ABSTRACT

The present invention describes the incorporation of liposomal gene constructs directly into a wound to further improve wound repair, or into wound coverage and/or closure materials to enhance the functionality of the material. The present invention further describes the use of human fetal membranes (e.g., amnion) enhanced with the liposomal gene therapy as a wound coverage material in full-thickness wound repair. The enhanced fetal membranes or enhanced cadaver skin have advantages over currently used materials lacking the liposomal gene construct and are an efficient and safe approach to improve clinical outcome in patients with burn injuries.

6 Claims, 16 Drawing Sheets

(2 of 16 Drawing Sheet(s) Filed in Color)

METHODS TO ENHANCE WOUND HEALING AND ENHANCED WOUND COVERAGE MATERIAL

CROSS-REFERENCE TO RELATED APPLICATIONS

This application claims benefit of priority of provisional application U.S. Ser. No. 60/140,196, filed Jun. 22, 1999, now abandoned.

BACKGROUND OF THE INVENTION

1. Field of the Invention

The present invention relates generally to the field of trauma medicine and wounds. More specifically the present invention relates to methods of enhancing wound healing and enhanced wound coverage materials.

2. Description of the Related Art

Burn injuries represent one of the most severe forms of trauma. The larger the burn injury, the more severe the consequences and the higher the chance of poor extended outcomes and death. There are over 2 million burn patients annually, and costs for treatment exceed one billion dollars a year. Fire and burn injuries are the third leading cause of injuries and death in children aged 1 to 18 years. The number of mortalities from burns has decreased over the last decade, primarily due to early and adequate fluid resuscitation, early and aggressive nutritional support, improved infection control, improved wound care/would healing, and hormonal modulation.

Wound healing is of major importance in the recovery of burn patients, and therefore, their clinical outcome. It has been shown that early wound excision and tissue grafting improved the hypermetabolic response and survival after burn injury. Autologous skin can be used to graft the excised wound (donor-site), however, this is not an effective treatment in patients with especially large burns. In these cases, synthetic skin materials or cadaver skin have been used.

Wound cover should be distinguished from wound closure. Wound closure materials are biologically accepted by the wound bed and become permanently incorporated into the healing wound. On the other hand, wound coverage materials rely upon incorporation into the wound coagulum and in-growth of granulation tissues for adhesion; this phenomenon is characteristic of many wound coverage materials. Wound coverage materials, in general, do not biodegrade, and therefore, can only be temporary substitutes for the epidermis. Wound coverage materials must therefore be replaced with the patient's skin, either by re-epithelialization or skin grafts. In the case of temporary coverage, the wound should not be colonized with bacteria and should be sufficiently superficial that it would be expected to heal completely within 3 weeks. Epithelial cells from the epidermal appendages grow and replace the destroyed epidermis, and gradually, the wound coverage material is shed. Therefore, the primary goal for the wound coverage materials in superficial second degree burns are to limit the microbial invasion of the wound bed (microbial barrier) to thereby prevent infection, and to limit the access of air to thereby minimize pain.

Wound coverage materials have also been used for deep second-degree or third-degree injuries prior to definitive wound closure with autologous skin in patients with massive burn injuries. The optimal wound coverage material has yet to be determined. However, the requirements for wound closure materials are to mimic normal dermis and epidermis. Specifically, the requirements of a superior wound closure material are: a) to provide a nontoxic, antiseptic, noninflammatory, and nonantigenic barrier to bacteria and other microbes; b) to provide a normal rate of heat and water conductivity; c) to provide an immediate, uniform and intimate adherence to the wound bed; d) to provide support for normal local host defense and wound repair mechanisms; e) to maintain elasticity and long-term durability; f) to allow growth potential; and g) to provide long-term mechanical and cosmetic function with wound contracture properties that are comparable to split thickness autografts.

INTEGRA™, ALLODERM™ or BIOBRANE™ demonstrate very good biocompatibility and healing characteristics. However, these materials are very expensive, which limits their widespread use. Cadaver skin is a relatively efficient and cheap approach for wound coverage. However, the risk of transmission of HIV, CMV, HSV and hepatitis is a significant concern, and therefore, limits application of cadaver skin.

Fetal membranes possess numerous advantageous characteristics which make this material applicable as wound coverage material, including: a) low immunogenicity; b) nontoxic, antiseptic and noninflammatory; c) no HIV, HSV or CMV infection; d) unlimited quantities (which, therefore, allow fetal membrane tissue to be an inexpensive alternative to existing skin replacements); e) variability of length, diameter and thickness; and f) endogenous mechanical components, such as collagen, laminin and fibronectin, to thus ensure mechanical stability, growth support and potential similar to that of normal human skin.

Biochemically, thermal injury is a particularly severe form of trauma accompanied by a hypermetabolic response characterized by high cardiac output, increased oxygen consumption, compromised immune response and protein and fat catabolism [34]. The burn wound supports this vulnerable hypermetabolic state by producing and releasing thromboxane and pro-inflammatory cytokines [35–37]. Wound healing is thus important to survival and recovery in burn patients [22,38–39]. Anabolic agents, such as growth hormone and insulin-like growth factor-I, have been shown to attenuate the hypermetabolic response and to improve wound healing [35,39–41].

Insulin-like growth factor-I, a small polypeptide approximately 7.5 kD in size, is an anabolic agent that has been shown to improve metabolism [35], gut mucosal function [42] and protein losses [43] after a thermal injury. IGF-I mediates the actions of growth hormone in the hypermetabolic state by attenuating lean body mass loss, the compromised immune response, the acute phase response, and by enhancing wound healing [35,38,44–47]. IGF-I treatment improves wound healing by stimulating collagen formation and the mitogenicity of fibroblasts and keratinocytes [40, 41,48]. There are adverse side effects, such as hypoglycemia, mental status changes, edema, fatigue and headache, which limit the therapeutic utility of IGF-I in the treatment of burns [49,50]. These adverse side effects are most likely due to supra-physiological doses of free IGF-I, which are required for biological efficacy [49,50].

Selection of an appropriate vehicle for gene delivery is paramount [1,2]. Viruses, in particular adenoviruses due to their specific transfection capabilities, have been used as gene delivery vehicles [1–3]. Viruses, however, display viral infection-associated toxicity, immunological compromise, and possible mutagenic or carcinogenic effects that make this approach potentially dangerous [1]. Using liposomes as a delivery system thus becomes an attractive model due to their non-viral composition, stability, and ability to interact with the cell membrane [4]. The addition of cationic properties to the standard liposomal structure and incorporation of cholesterol, together with the use of cytomegalovirus (CMV) promoters into the cDNA constructs used for gene transfer, increase the efficacy and levels of transgenic expression equal to those achieved with adenoviral constructs [4,5].

The prior art is deficient in methods to enhance wound healing and enhanced wound coverage materials. The present invention fulfills this long-standing need and desire in the art.

SUMMARY OF THE INVENTION

The present invention describes a method of enhanced wound healing using liposomes carrying genes encoding growth-enhancing agents. The present invention further describes an enhanced wound coverage material impregnated with liposomes carrying genes expressing growth factors to improve wound healing. It is an object of the present invention to decrease the hypermetabolic response, and thus, improve the clinical outcome and increase the survivability after trauma, particularly thermal injury.

The present invention describes the incorporation of liposomal gene constructs directly into a wound and/or into the coverage material to improve wound repair and enhance the functionality of the wound coverage material. The present invention further describes the use of enhanced fetal human amnion membrane, in conjunction with liposomal gene constructs expressing growth factors, as a transient wound coverage material in full-thickness wound repair. Fetal membrane has advantages over currently used materials, such as Integra™, Biobrane™, Alloderm™, and is an efficient and safe approach to improve clinical outcome.

One object of the present invention is to provide methods to enhance wound healing, methods to enhance wound coverage material and an enhanced wound coverage material.

In an embodiment of the present invention, there is provided a method of enhancing wound healing, comprising the step of: injecting into the wound a liposome, wherein the liposome comprises at least one gene encoding a growth-enhancing agent.

In another embodiment of the present invention, there is provided a method of enhancing wound healing, comprising the steps of: covering the wound with a wound coverage material, wherein the wound coverage material is impregnated with a liposome, wherein the liposome comprises at least one gene encoding a growth-enhancing agent.

In yet another embodiment of the present invention, there is provided a method of enhancing wound healing, comprising the steps of: covering the wound with a wound closure material, wherein the wound closure material is impregnated with a liposome, wherein the liposome comprises at least one gene encoding a growth-enhancing agent.

In still yet another embodiment of the present invention, there is provided an enhanced wound dressing, comprising: a wound coverage material; and a liposome comprising at least one gene encoding a growth-enhancing agent.

In another embodiment of the present invention, there is provided a composition for enhancing wound healing, comprising: a liposome, wherein the liposome comprises at least one gene encoding a growth-enhancing agent; and a pharmaceutically acceptable carrier.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Figure 1:
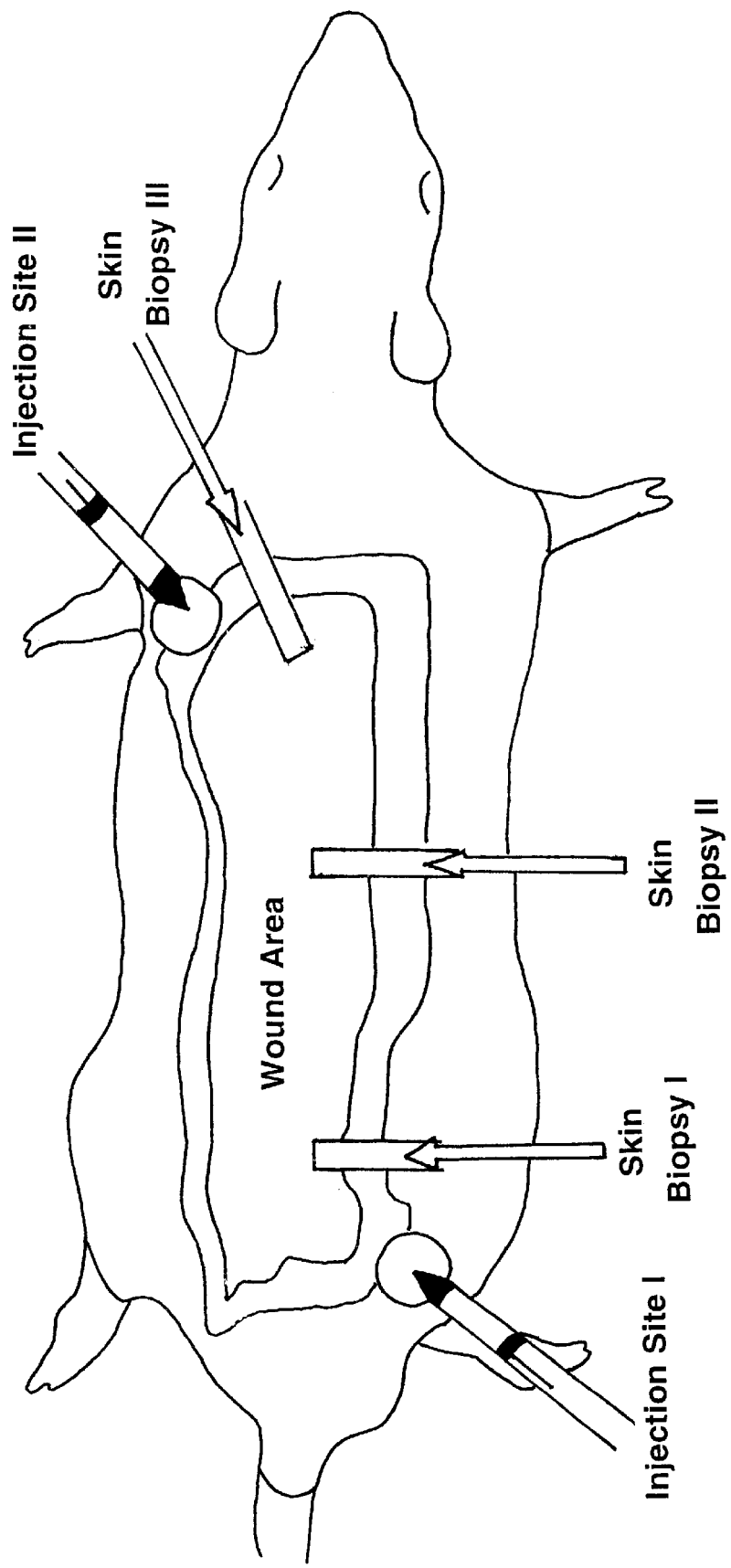
FIG. 1 shows a schematic cartoon of the injection sites. Animals with one injection site received the injection only at injection site I, whereas animals with 2 injections received the injections at injection sites I and II. Skin biopsies I, II and III were taken for analysis 33 days after burn.

The present invention demonstrates the advantages of using liposomally-delivered vectors expressing growth-enhancing agents to trauma wounds, particularly thermal injuries, in rats. The present invention further compares the functionality of various wound coverage materials, such as fetal membrane, human skin and several commercially available synthetic materials in Yorkshire mini-pigs.

More specifically, the present invention describes the introduction of liposomal gene constructs coding for growth-enhancing factors, e.g., insulin-like growth factor-I (IGF-I), or keratinocyte growth factor (KGF) directly into the wound bed or into the wound coverage material and compares the efficacy to non-liposomal-treated wounds. Efficacy of the liposomal gene therapy is assessed by measuring the take rate and healing time, examining wound contraction histologically, histology, immune markers of coverage material rejection and the extent of the hypermetabolic response at weekly intervals over a 4 month period.

Based on the findings reported herein, gene therapy, in which one or more genes expressing growth factor(s) are delivered via liposome vehicles injected directly into the wound or injected into a wound coverage material which is subsequently applied to the wound will reform and enhance the current treatment for thermal injuries, skin ulcers and skin grafting procedures.

The present invention is directed towards methods of enhancing wound healing and enhanced wound coverage materials.

The present invention is also directed to a method of enhancing wound healing, comprising the step of: injecting into the wound a liposome, wherein the liposome comprises at least one gene encoding a growth-enhancing agent.

The present invention is also directed to a method of enhancing wound healing, comprising the steps of: covering the wound with a wound coverage material, wherein the wound coverage material is impregnated with a liposome, wherein the liposome comprises at least one gene encoding a growth-enhancing agent.

In yet another aspect, the present invention is also directed to a method of enhancing wound healing, comprising the steps of: covering the wound with a wound closure material, wherein the wound closure material is impregnated with a liposome, wherein the liposome comprises at least one gene encoding a growth-enhancing agent.

In yet another aspect, the present invention is also directed to an enhanced wound dressing, comprising: a wound coverage material; and a liposome comprising at least one gene encoding a growth-enhancing agent. Typically, the liposome comprising the growth-enhancing agent is delivered to the wound coverage material by injection, which may be done prior to or subsequent to applying the wound coverage material to the wound.

In yet another aspect, the present invention is also directed to a composition for enhancing wound healing, comprising: a liposome, wherein the liposome comprises at least one gene encoding a growth-enhancing agent; and a pharmaceutically acceptable carrier. The composition of this embodiment may be packaged such that the composition can be readily loaded into a syringe, or alternately, may be packaged directly in a syringe.

In these embodiments, representative wounds which may be treated using the compositions and methods of the present invention include thermal trauma, chemical trauma, excisional trauma, surgical trauma or abrasion. Preferable liposomes are cholesterol-containing cationic liposomes. Generally, growth-enhancing agents are growth hormone, insulin-like growth factor-I, keratinocyte growth factor, fibroblast growth factor, epidermal growth factor, platelet derived growth factor or transforming growth factor-β. Preferably, when the growth-enhancing agent is insulin-like growth factor-I (IGF-I), and the concentration of the gene encoding the IGF-I in the liposome is about 2.2 µg/ml liposome.

Representative wound coverage materials include human fetal amnion, human fetal chorion, human cadaver skin, synthetic skin, and other materials known to those having ordinary skill in this art. Representative wound closure materials include human fetal amnion, human fetal chorion, human syngeneic skin, human allogeneic skin, and other materials known to those having ordinary skill in this art.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e. g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a speciicf gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

In general, "gene" is intended to include promoter and regulatory elements operably linked to a coding sequence. Those promoter sequences and regulatory elements may be the gene's natural promoter and/or regulatory elements, or they may be heterologous. A "heterologous" region is an identifiable segment of DNA within a larger DNA molecule that is not found in association with the larger molecule in nature. Thus, when the heterologous region encodes a mammalian gene, the gene will usually be flanked (e.g., promoter sequences and/or regulatory elements) by DNA that does not flank the mammalian genomic DNA in the genome of the source organism. In another example, the coding sequence is a construct where the coding sequence itself is not found in nature (e.g., a cDNA in which the genomic coding sequence contains introns, or synthetic sequences having codons different than the native gene). Allelic variations or naturally-occurring mutational events do not give rise to a heterologous region of DNA as defined herein.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "amnion" refers to an extraembryonic thin membrane surrounding the embryo and derived from ectoderm and mesoderm tissues.

As used herein, the term "chorion" refers to the outermost extraembryonic membrane which eventually becomes part of the placenta, where in addition to respiratory functions, it supplies nutrients and removes waste.

As used herein, the term "liposome" refers to a small vesicle bounded by a bilayer lipid membrane made artificially from phospholipids. DNA, proteins and other materials can be enclosed within the liposome and introduced into animal cells by fusion with the plasma membrane. As used herein, the term "cholesterol-cationic liposome" refers specifically to a cholesterol-containing liposome.

As used herein, the term "growth-enhancing agent" refers to compounds that promote growth.

As used herein, the term "take rate" refers to the 'healthy rate', or 'acceptance rate' of the donor tissue onto the host tissue.

It is specifically contemplated that pharmaceutical compositions may be prepared using the liposomes described in the present invention. In such a case, the pharmaceutical composition comprises a gene encoding a growth factor, the liposome of the present invention and a pharmaceutically acceptable carrier. A person having ordinary skill in this art would readily be able to determine, without undue experimentation, the appropriate dosages and routes of administration of the liposome of the present invention. When used on a patient in therapy, the liposome vehicle described in the present invention is administered to the patient or an animal in therapeutically effective amounts, i.e., amounts that effectively deliver appropriate amounts of the DNA encoding a growth-enhancing agent. It will normally be administered in injectable form to the wound or wound coverage material, but other routes of administration will be used as appropriate. The dose and dosage regimen will depend upon the nature of the wound (the severity of the tissue damage) and its size, the patient's history and other factors. The amount of liposome administered will typically be based upon wound area, with liposomal injections approximately 4 cm apart. The schedule will be continued to optimize effectiveness while balanced against negative effects of treatment. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press; which are incorporated herein by reference. For local administration, the liposomes will most typically be formulated in a unit dosage injectable form (solution, suspension, emulsion) in association with a pharmaceutically acceptable carrier. Such carrier are preferably non-toxic and non-therapeutic. Examples of such carrier are water, saline, Ringer's solution, dextrose solution, and 5% human serum albumin. Nonaqueous carriers such as fixed oils and ethyl oleate may also be used. The carrier may contain minor amounts of additives such as substances that enhance isotonicity and chemical stability, e.g., buffers and preservatives. The liposomes will typically be formulated in such carriers at concentrations of about 1 $\mu$g to 10 $\mu$g.

The following examples are given for the purpose of illustrating various embodiments of the invention and are not meant to limit the present invention in any fashion:

EXAMPLE 1
Experimental Animals—Rats

Adult male Sprague-Dawley rats (350–375 g) were placed in wire bottom cages and housed in a temperature-controlled room with a 12 hour light-dark cycle. The animals were acclimatized to their environment for 7 days prior to the start of the blinded study. All received equal amounts of a liquid diet of Sustacal (Mead Johnson Nutritionals, Evansville, Ind., USA) and water ad libitum throughout the study. Each rat received a 60% total body surface area (TBSA) full-thickness scald burn. Thermally injured rats were then randomly divided into:

(a) 2 groups to receive injections of cholesterol-containing cationic liposomes (20 $\mu$l liposomes in 180 $\mu$l saline, n=28), or saline (control, 200 $\mu$l, n=28);

(b) 2 groups to receive weekly subcutaneous injections of liposomes (10 $\mu$l liposomes in 180 $\mu$l saline) containing 2.2 $\mu$g of an IGF-I cDNA construct and 0.2 $\mu$g of the reporter gene $\beta$-galactosidase, Lac Z cDNA construct driven by a CMV promoter (n=12) at one injection site on the edge of the burn wound (FIG. 1), or weekly subcutaneous injections of liposomes (10 $\mu$l liposomes in 180 $\mu$l saline) containing 2.2 $\mu$g cytomegalovirus driven IGF-I cDNA construct and 0.2 $\mu$g of the reporter gene for $\beta$-galactosidase, Lac Z cDNA (n=12) at two injection sites on the edge of the burn wound (FIG. 1); or (c) 3 groups to receive weekly subcutaneous injections of saline (200 $\mu$l normal saline; n=10); weekly subcutaneous injections of liposomes (10 $\mu$l liposomes in 180 $\mu$l saline) containing 0.2 $\mu$g of the reporter gene for $\beta$-galactosidase LacZ cDNA construct (n=10); or weekly subcutaneous injections of liposomes (10 $\mu$l liposomes in 180 $\mu$l saline) containing 2.2 $\mu$g of an IGF-I cDNA construct and 0.2 $\mu$g of the reporter gene $\beta$-galactosidase LacZ cDNA construct (n=10).

EXAMPLE 2
Experimental Animals—Pigs

The wound repair mechanisms in Yorkshire mini-pigs are closest to the same mechanisms in humans. Thus, Yorkshire mini-pigs are a well-described model and have been used in several experimental trauma studies. Each of 10 Yorkshire swines receive 4 full-thickness wounds (standard model) under anesthesia and analgesia. Each wound site is square or rectangular in shape, with an approximate dimension of 8×8 cm, spaced approximately 5 cm between sites and confined to the area of the upper flank and back. The wounds must be positioned and placed according to a particular scheme such that the animal can lie comfortably on its side following release from the restraining hammock.

Immediately after wound induction, the wound is covered with human fetal chorion/amnion, INTEGRA™ (Life Science), ALLODERM™ (Life-Cell) or BIOBRANE™ (Dow-Hickhan). The cover is stapled to the unburned wound and covered with triple-antibiotic ointment-impregnated gauze and a bulky pressure dressing. Staples and/or sutures are used as required.

Following surgery, the study animals are suspended in a hammock restraint while recovering from anesthesia so as to protect graft sites from injury or dislodgement. The animals remain in this hammock restraint for no more than 24 hours.

EXAMPLE 3
Liposomes

Figure 2:
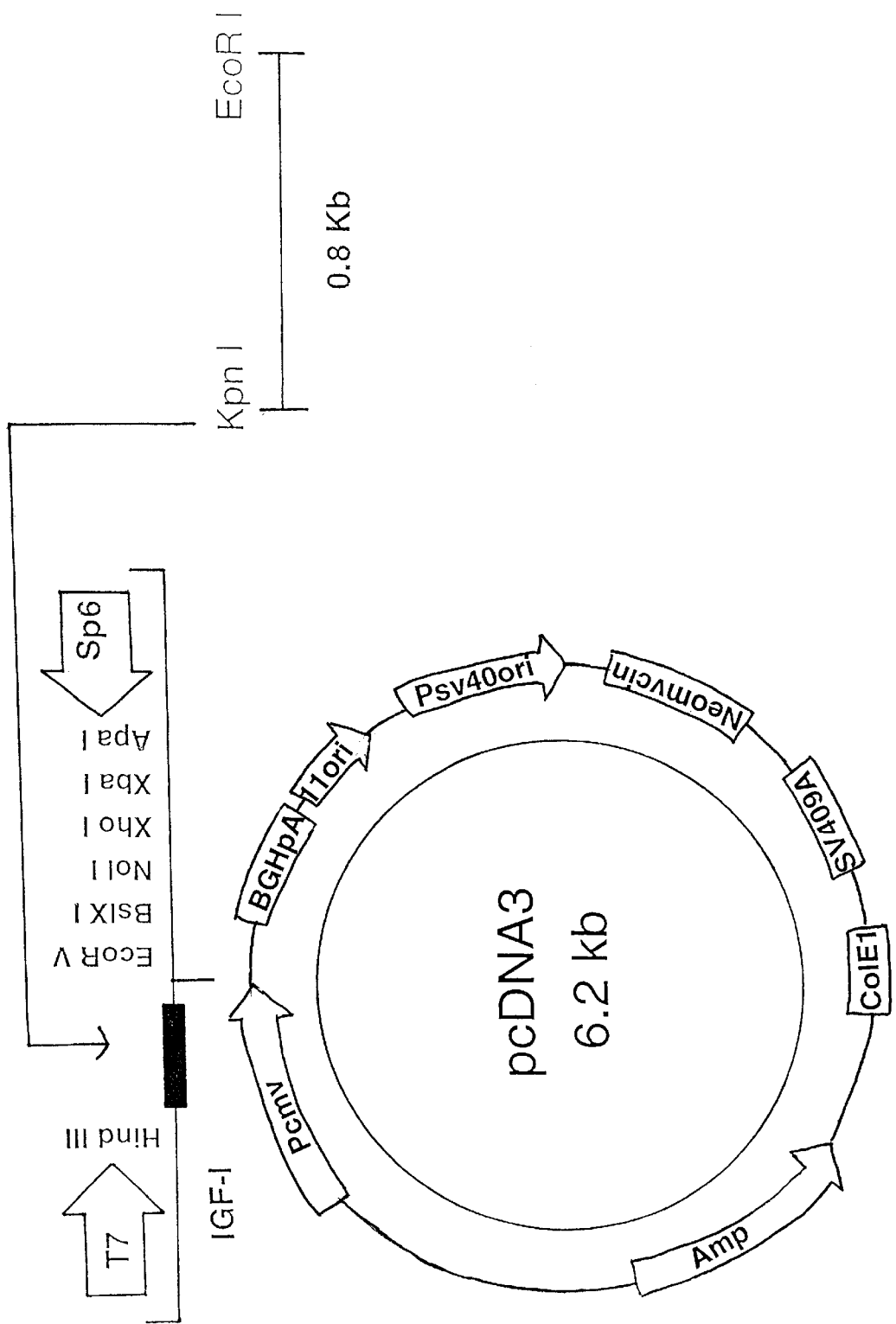
FIG. 2 shows a schematic of the IGF-I plasmid (pcDNA3) cDNA with the CMV-driven promoter. A structurally similar plasmid for β-galactosidase (Lac Z gene ) was also encapsulated into the same liposome.

The liposomes used were cholesterol-containing cationic liposomes, DMRIE-C Reagent (1,2-dimyristyloxypropyl-3-dimethyl-hydroxyl ethyl ammonium bromide) prepared with cholesterol membrane-filtered water (Life Technologies, Rockville, Md.). The IGF-I cDNA construct (FIG. 2) consisted of a cytomegalovirus driven IGF-I cDNA plasmid prepared at the UTMB Sealy Center for Molecular Science Recombinant DNA Core Facility (the IGF-I cDNA was a kind gift of G. Rotwein, NIH, Bethesda, Md.). The doses used were 10% liposomes (the highest concentration used in DNA transfer experiments that does not have deleterious consequences on DNA solubility and is compatible with gene transfer paradigms). In order to determine the time course of liposomal effects, liposomes were injected intravenously into the tail vein of rats in group (a) 0.5 h after the thermal injury and changes were examined over a 7-day period. The volume of 200 $\mu$l is an amount that can be administered into the tail vein of a rat without causing deleterious side effects, such as cardiac arrest. Immediately after the thermal injury, each rat in group (b) or (c) received 0.2 ml of the solutions injected at either one site, 1 cm from the wound margin, or at two sites distal to each other (FIG. 1). This protocol was repeated once a week for 4 weeks. Lipoplexes were prepared fresh every week prior to injections.

EXAMPLE 4

Protocol

Figure 3:
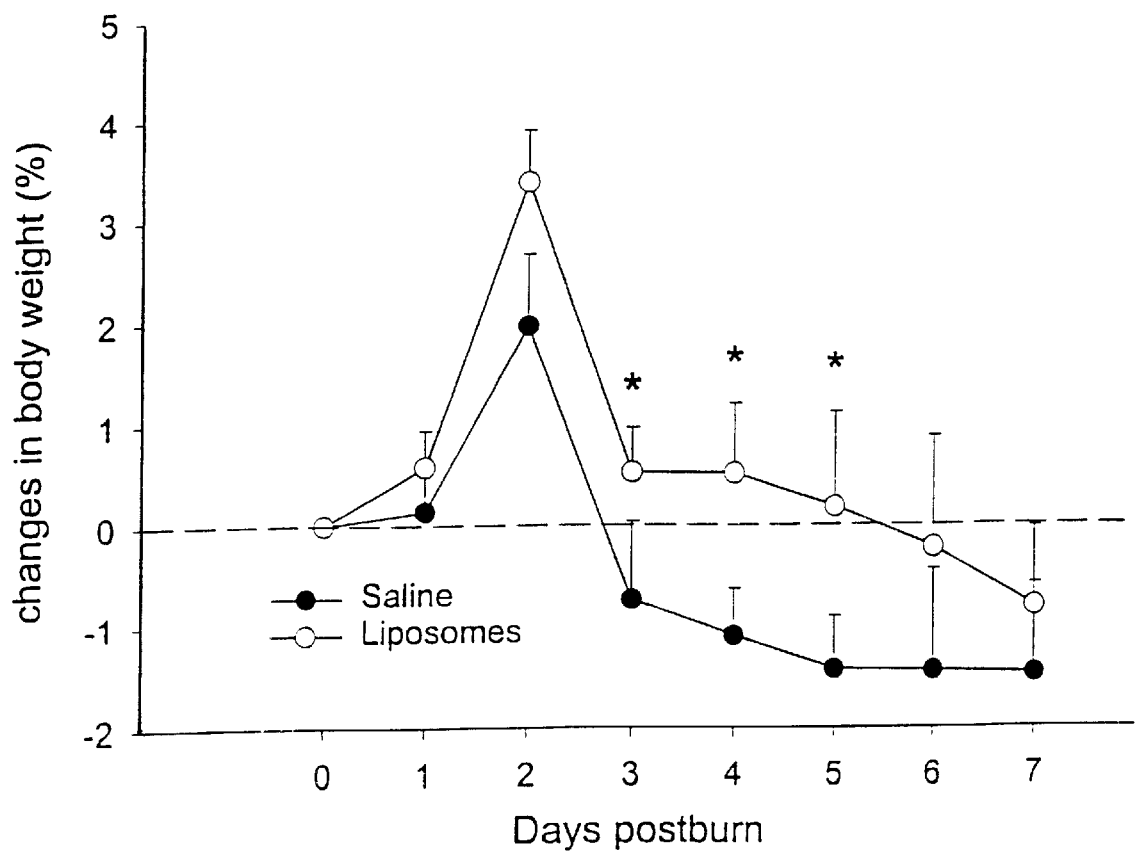
FIG. 3 shows percent change in body weights depicted for the 7 day study. * Significant difference between groups at $p<0.05$. Data are presented as means±SEM.

Body weights were measured at the same time each day. The percent change in total body weight generally increased during the first 2 days followed by a decrease in body weight 2 days postburn. Rats receiving liposomes maintained their body weight better compared to the saline-treated controls, p<0.05 (FIG. 3). Rats were sacrificed by decapitation 1, 2, 5 or 7 days after burn (for rats in group (a)), or alternatively, 5 days after the last injection (33 days after burn) for rats in groups (b) and (c). Blood was collected into serum and plasma separators, spun at 1000 g for 15 minutes, decanted, and frozen at −73° C. Liver and gastrocnemius muscle were harvested, weighed, sectioned and samples of each dried at 60° C. to a constant weight. The dry/wet weight ratios were used to estimate protein content. Three dorsal skin samples, defined as biopsy I, II or III, were harvested, snap frozen in liquid nitrogen and stored at −73° C. for analysis (FIG. 1). There were no differences in dry/wet weight ratios between liposome-treated and control animals for gastrocnemius muscle and liver.

Serum cholesterol, free fatty acids, serum acute phase proteins (haptoglobin and $\alpha_2$-macroglobulin), constitutive hepatic proteins (total protein, transferrin and albumin), and glucose were measured on a Behring nephelometer (Behring, Dearfield, Ill.). Serum $\alpha_1$-acid glycoprotein was determined by ELISA (Wako Chemicals Inc., Richmond, Va.). A standard curve for rat $\alpha_1$-acid glycoprotein concentrations was linear from 0 to 1500 pg/ml on a logarithmic scale. Plasma TNF-$\alpha$ levels were determined by ELISA (Endogen, Woburn, Mass.). The standard curve used for the quantification of rat TNF-$\alpha$ was linear from 0 to 833 pg/ml on a logarithmic scale. Serum IL-1$\beta$ levels were determined by ELISA (Biosource Int., Camarillo, Calif.) and its standard curve used for the quantification of rat IL-1$\beta$ was linear from 0 to 1500 pg/ml on a logarithmic scale. Serum IL-6 was determined by bioassay using log phase B9 cells (mouse hybridoma line) treated with increasing serum concentrations. Cell proliferation in response to additional serum was measured by quantitative MTS reduction spectrophotometrically.

EXAMPLE 5

Transfection

Transfection was determined by measuring the presence of $\beta$-galactosidase. $\beta$-galactosidase protein was detected by histochemical staining with Bluo-gal in the three skin biopsies. Skin specimens were fixed overnight at 4° C. in fixative consisting of 4% paraformaldehyde in a HEPES-buffered Hanks solution at pH 7.6. After washing in buffer and phosphate-buffered saline (PBS), the specimens were incubated overnight at 37° C. in a 0.1% solution of Bluo-Gal substrate (halogenated indolyl-$\beta$-D-galactoside) (LIFE Technologies, Gaithersburg, Md., USA), buffered to pH 7.6. After extensive washing, tissues were embedded in paraffin, and histologic sections made and stained with hematoxylin and eosin or with eosin alone.

The presence of $\beta$-galactosidase protein was also detected by chemiluminescent reporter gene assay (GALACTO-LIGHT PLUS™, Tropix Inc. Bedford, Mass. USA) in skin. Samples were prepared as follows [55]: 100 mg tissue was homogenized in 200 µl of Lysis buffer (40 mM Tris (pH 7.5), 1 mM EDTA, 150 mM NaCl) for approximately 30 seconds. Samples were centrifuged (12,000×g) for 3 minutes. The supernatant was removed, the volume measured and stored on ice. The residual pellet was rinsed with 200 µl lysis buffer and micro-centrifuged. The assay followed manufacturers directions in 96 well plates.

Figure 4A:
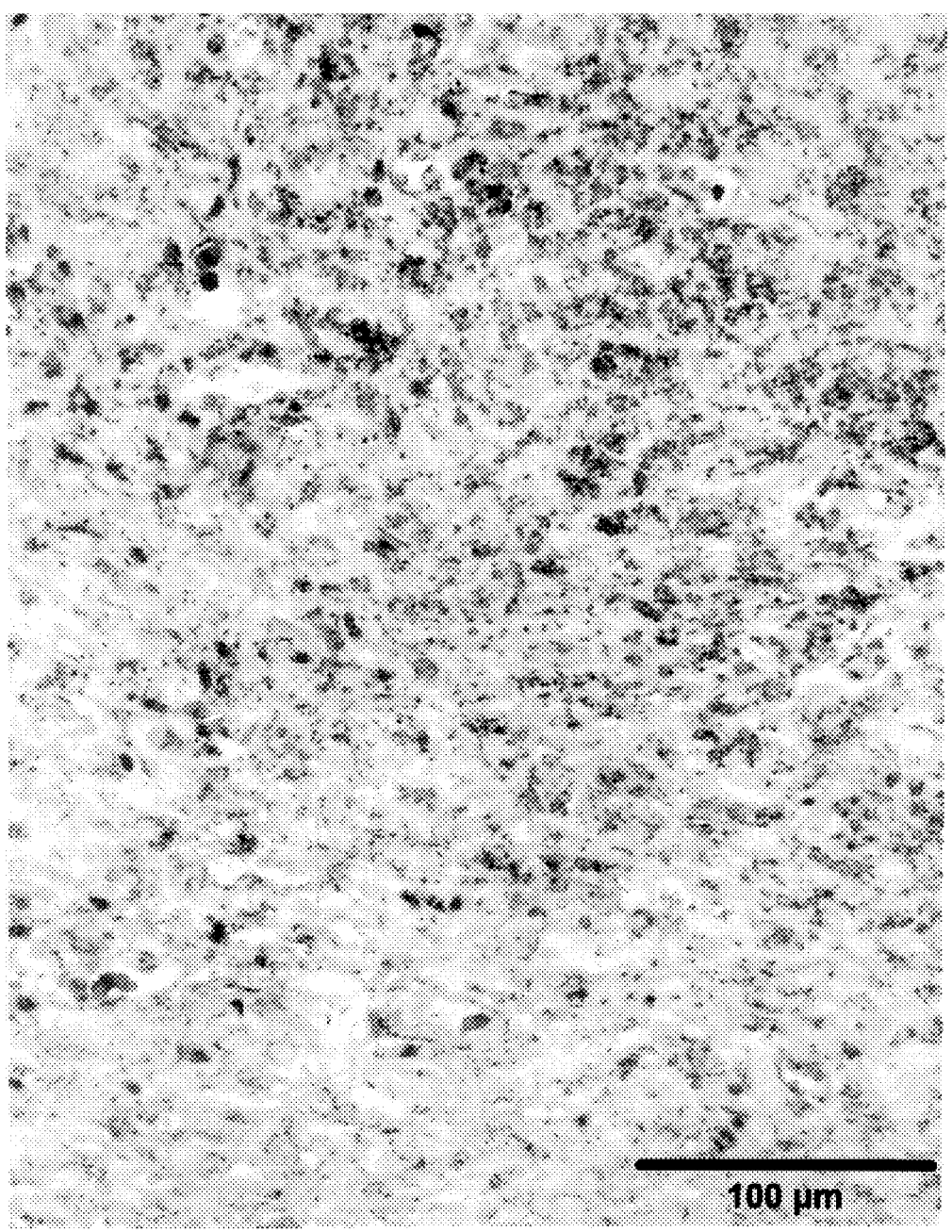
FIGS. 4A and 4B show histologic sections of skin after histochemical reaction for β-galactosidase activity and counterstained with eosin. (4A). A finely granular blue-green reaction product is present within many myofibroblastic and histiocytic cells in the granulation tissue underlying the burn wound. Magnification ×380. (4B). Saline-injected (control) dermal tissue underlying uninjured skin near the burn wound showed no reaction product. Magnification ×380.
Figure 4B:
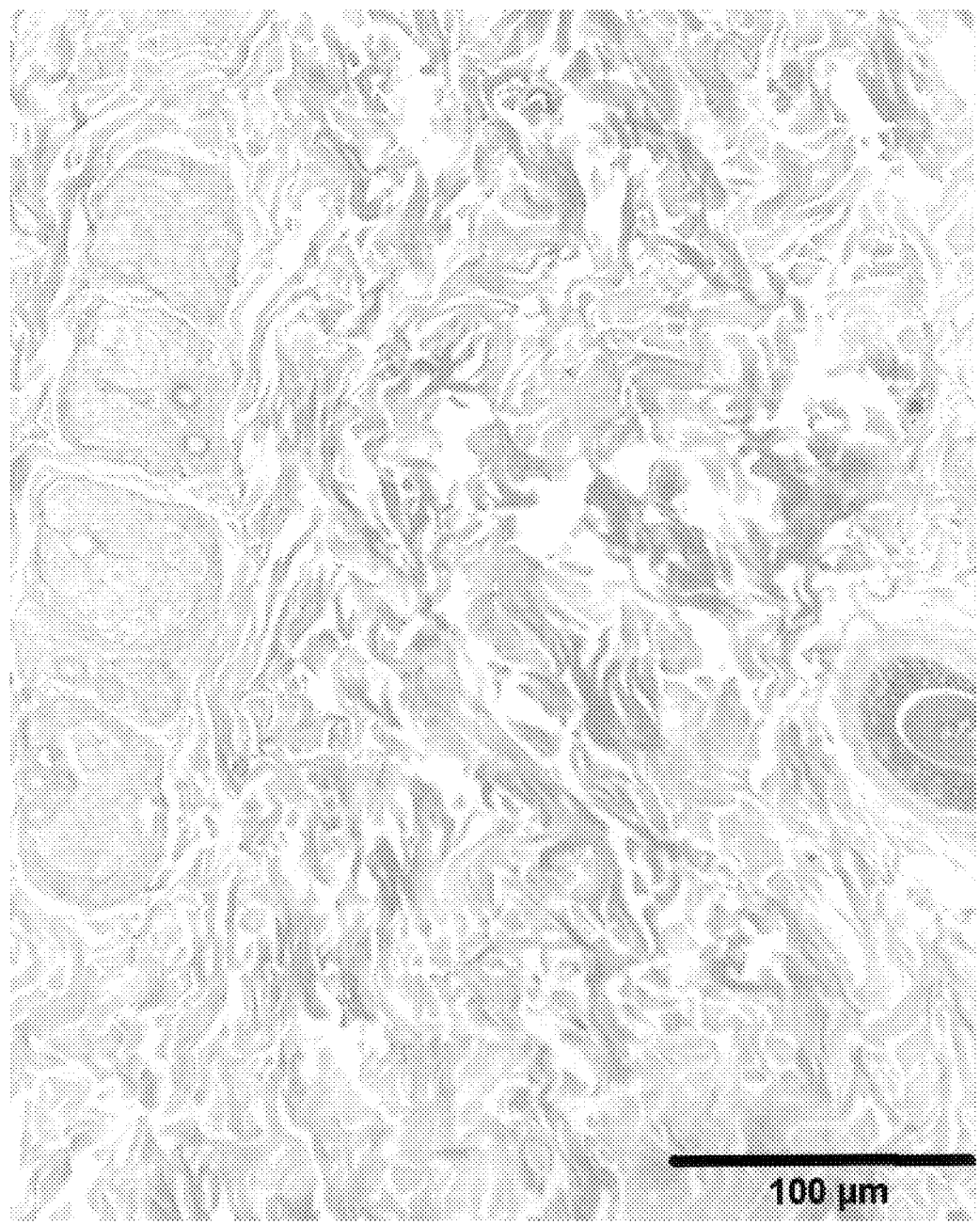

The fine granular blue-green reaction product of the $\beta$-galactosidase reaction was predominantly present in the granulation tissue, composed of spindle-shaped myofibroblasts, macrophages, and growing small blood vessels underlying the wound. The cells consistently staining for $\beta$-galactosidase were myofibroblasts, endothelial cells, and macrophages in the areas of inflammation and included multinucleate giant cells, indicating preferential transfection of cells with higher proliferation rates (FIG. 4A). Although most staining for $\beta$-galactosidase was in the cytoplasm, some reaction products were observed outside the cell boundaries, possibly due to enzymes released by dead cells or the simple diffusion of reaction products. A small amount of reaction product was also detected in the matrix of hair follicles near the injection sits. No $\beta$-galactosidase was detected in saline-treated animals (FIG. 4B).

$\beta$-galactosidase protein expression was increased around the wound perimeter in rats receiving liposome-encapsulated LacZ cDNA plus IGF-I cDNA constructs compared to saline treated rats (p<0.05; Table 1). There was no difference amoung groups in $\beta$-galactosidase concentrations in blood cells, liver, spleen or kidney. This finding is consistent with the conclusion that systemic cells were not transfected after subcutaneous cDNA injections (Table 2).

TABLE 1

$\beta$-galactosidase expression in skin

| | $\beta$-galactosidase (counts/second/ml extract) | | |
|---|---|---|---|
| Site of skin biopsy | Saline (n = 10) | Liposome (n = 10) | IGF-I cDNA (n = 10) |
| I | 2503 ± 366* | 5568 ± 381 | 5620 ± 509 |
| II | 2858 ± 556* | 5267 ± 325 | 6555 ± 811 |
| III | 2982 ± 664* | 6023 ± 800 | 7357 ± 1042 |

Data presented are mean ± SEM.
*Significant differences vs. liposomes and IGF-I cDNA (p < 0.05).

TABLE 2

$\beta$-galactosidase expression in blood, liver, kidney and spleen

| | $\beta$-galactosidase (counts/second/ml extract) | | |
|---|---|---|---|
| Tissue | Saline (n = 10) | Liposomes (n = 10) | IGF-I cDNA (n = 10) |
| Blood | 349 ± 37 | 235 ± 48 | 244 ± 116 |
| Liver | 1757 ± 139 | 1881 ± 956 | 1620 ± 886 |
| Kidney | 964 ± 90 | 896 ± 100 | 916 ± 98 |
| Spleen | 1154 ± 217 | 1460 ± 348 | 886 ± 379 |

Data presented as mean ± SEM.

EXAMPLE 6

IGF-I

Figure 5:
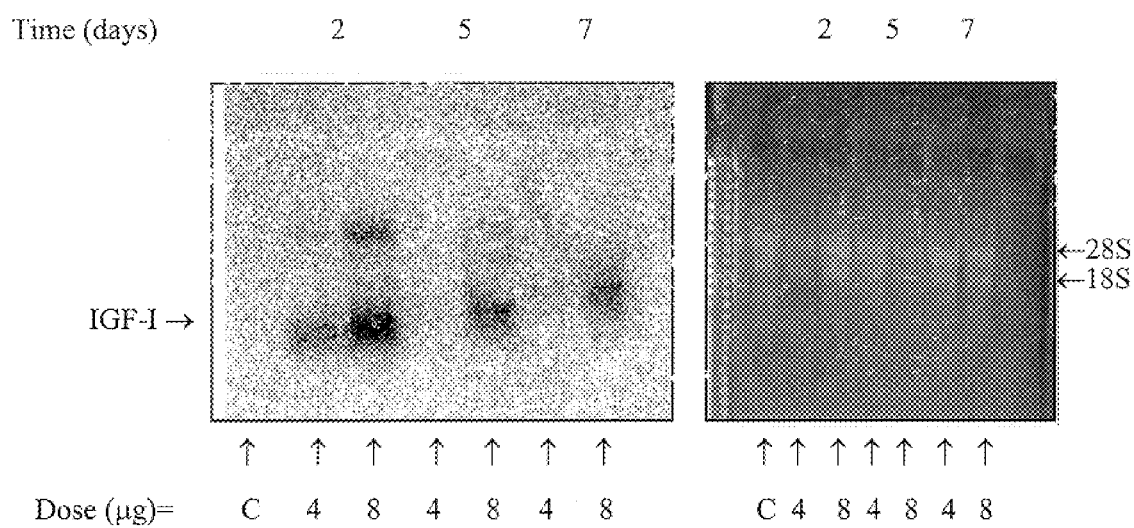
FIG. 5 shows the presence of IGF-I mRNA in the skin after transfection with lipoplexees containing the cDNA coding for IGF-I. No IGF-I mRNA could be detected in skin biopsies from rats transfected with liposomes alone or saline (Lanes A and B). There was a significant amount of IGF-I mRNA in skin biopsies from rats transfected with IGF-I cDNA (lane C). Representative sample is shown.

In rats receiving the IGF-I cDNA construct, there was evidence of IGF-I mRNA in the skin proximal to transfection sites but not in control or sham-treated tissues (FIG. 5).

IGF-I protein concentrations were measured by RIA in the three skin biopsies (FIG. 1). Proteins were extracted by pulverizing approximately 40 mg of tissue under liquid nitrogen, adding extraction buffer (PBS⁻, 0.25 ml PMSF, 50 mg leupeptin, 100 mg aprotinin, and 50 mg antipain) in a volume 1:7 (7 ml buffer/gram tissue) and homogenizing the mixture. To allow proteins to recover, samples were frozen overnight at −80° C. After thawing, 50 µl of the homogenate was added to 150 µl of extraction solution and centrifuged at 13,500 rpm for 5 minutes. 100 µl of supernatant was added to 400 µl of neutralization solution, and the RIA performed as described in the kit guidelines (Diagnostic System Laboratories, Webster, Tex., USA).

In all skin biopsies taken, animals treated with the IGF-I cDNA constructs had higher IGF-I protein concentrations around the wound perimeter compared to biopsies from animals treated with liposomes alone or saline ($p<0.05$; Table 3). There was no difference among groups in IGF-I protein concentration in serum, liver, spleen or kidney (Table 4).

TABLE 3

IGF-I protein concentration in skin

| Site of skin biopsy | IGF-I protein (ng/ml) | | |
|---|---|---|---|
| | Saline (n = 10) | Liposomes (n = 10) | IGF-I cDNA (n = 10) |
| I | 94 ± 5 | 118 ± 10 | 174 ± 12* |
| II | 96 ± 11 | 113 ± 11 | 171 ± 13* |
| III | 98 ± 6 | 100 ± 5 | 178 ± 14* |

Data presented as mean ± SEM.
*Significant difference vs. Liposomes and saline, $p < 0.05$.

TABLE 4

IGF-I protein concentration in blood, liver, kidney and spleen

| Tissue | IGF-I protein (ng/ml) | | |
|---|---|---|---|
| | Saline (n = 10) | Liposomes (n = 10) | IGF-I cDNA (n = 10) |
| Blood | 139 ± 2 | 132 ± 5 | 135 ± 5 |
| Liver | 177 ± 3 | 181 ± 6 | 172 ± 6 |
| Kidney | 188 ± 4 | 186 ± 12 | 188 ± 8 |
| Spleen | 160 ± 3 | 150 ± 7 | 156 ± 6 |

Data presented as mean ± SEM.

EXAMPLE 7
Constitutive Hepatic Proteins, Acute Phase Proteins and Cytokines

Figure 6:
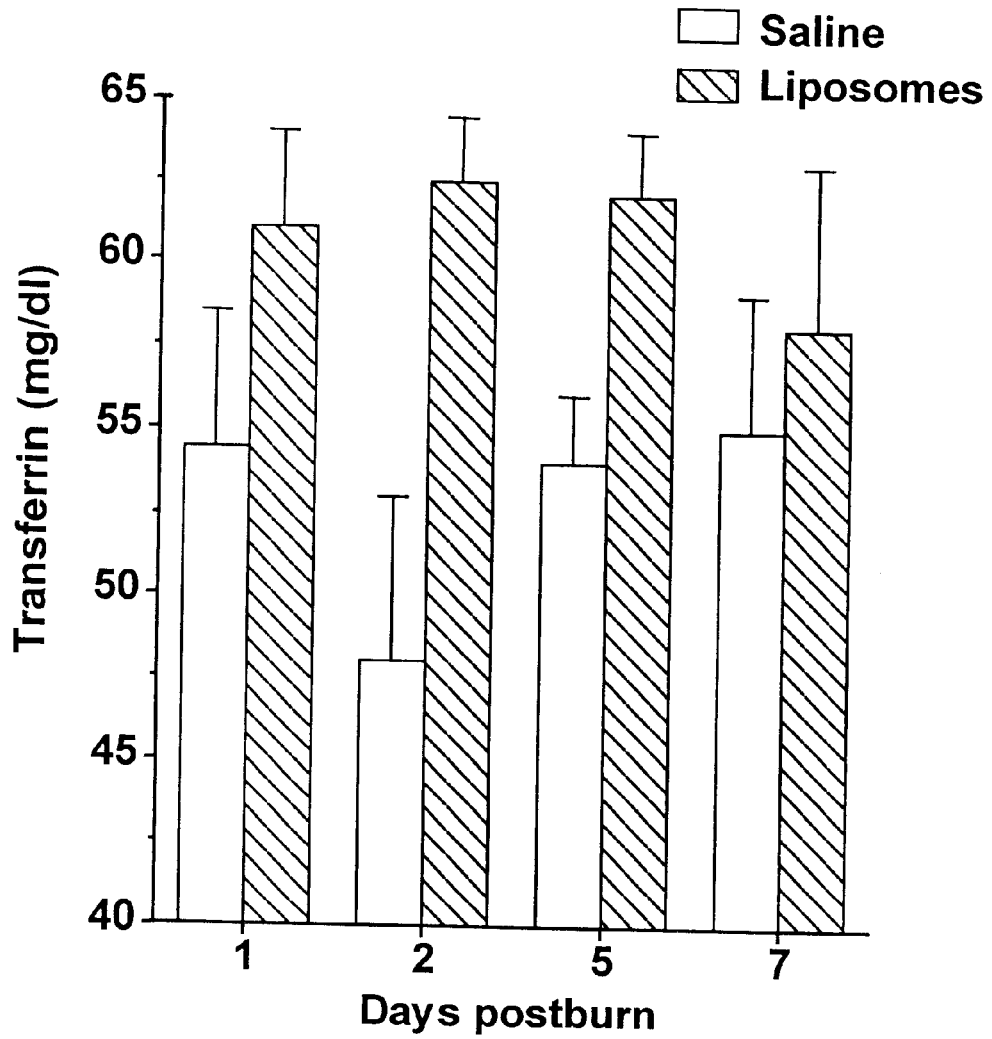
FIG. 6 shows serum transferrin concentrations during the 7 day study period. Serum transferrin decreased after burn injury. Liposomes attenuated the drop at 2 and 5 days postburn. * Significant difference between groups, $p<0.05$. Data presented as means±SEM. (Normal serum transferrin:>72 mg/dl).

Serum total protein concentration decreased after burn injury. Rats receiving liposomes showed an increase in serum total protein 5 days after burn (liposomes: 5.6±0.1 g/dl vs. controls: 5.2±0.1 g/dl), $p<0.05$. Serum transferrin decreased after burn injury by nearly 30% below normal. Rats treated with liposome showed an increase in serum transferrin at 2 and 5 days postburn compared to controls ($p<0.05$; FIG. 6). There were no significant differences in serum albumin between the treated and control groups. Furthermore, no significant differences between treated and control animals in serum cholesterol, free fatty acid and glucose could be demonstrated throughout the study period.

Figure 7:
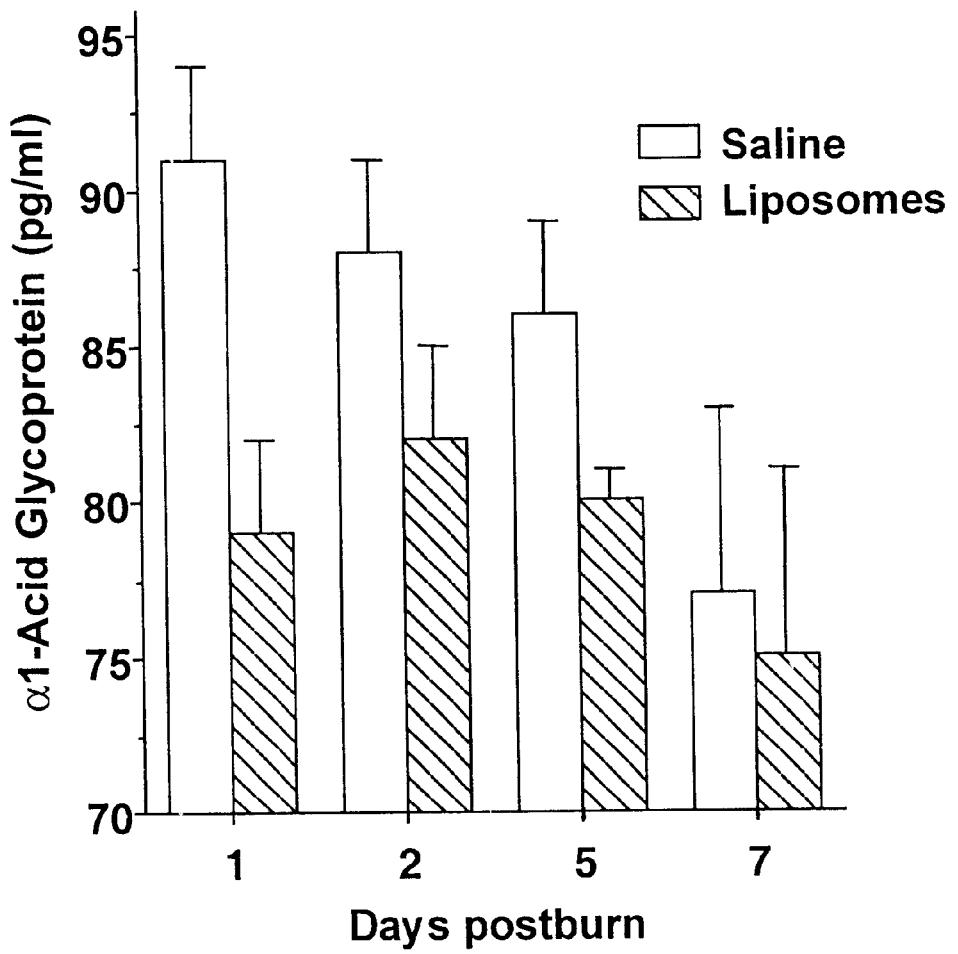
FIG. 7 shows serum $\alpha_1$-acidglycoprotein 1 to 7 days after thermal injury. * Significant difference between saline and liposomes at $p<0.05$. Data presented as means±SEM. (Normal serum $\alpha_1$-acidglycoprotein: 55–70 pg/ml).

Type I acute phase proteins, serum haptoglobin and $\alpha_1$-acid glycoprotein increased after thermal injury. Liposomes decreased serum $\alpha_1$-acid glycoprotein 1 and 5 days postburn ($p<0.05$; FIG. 7). There were no significant differences in serum haptoglobin between liposome-treated animals and controls. Type II acute phase protein increased after burn by nearly 50%. There were no differences in serum $\alpha_2$-macroglobulin between liposome-treated animals and control animals.

Figure 8:
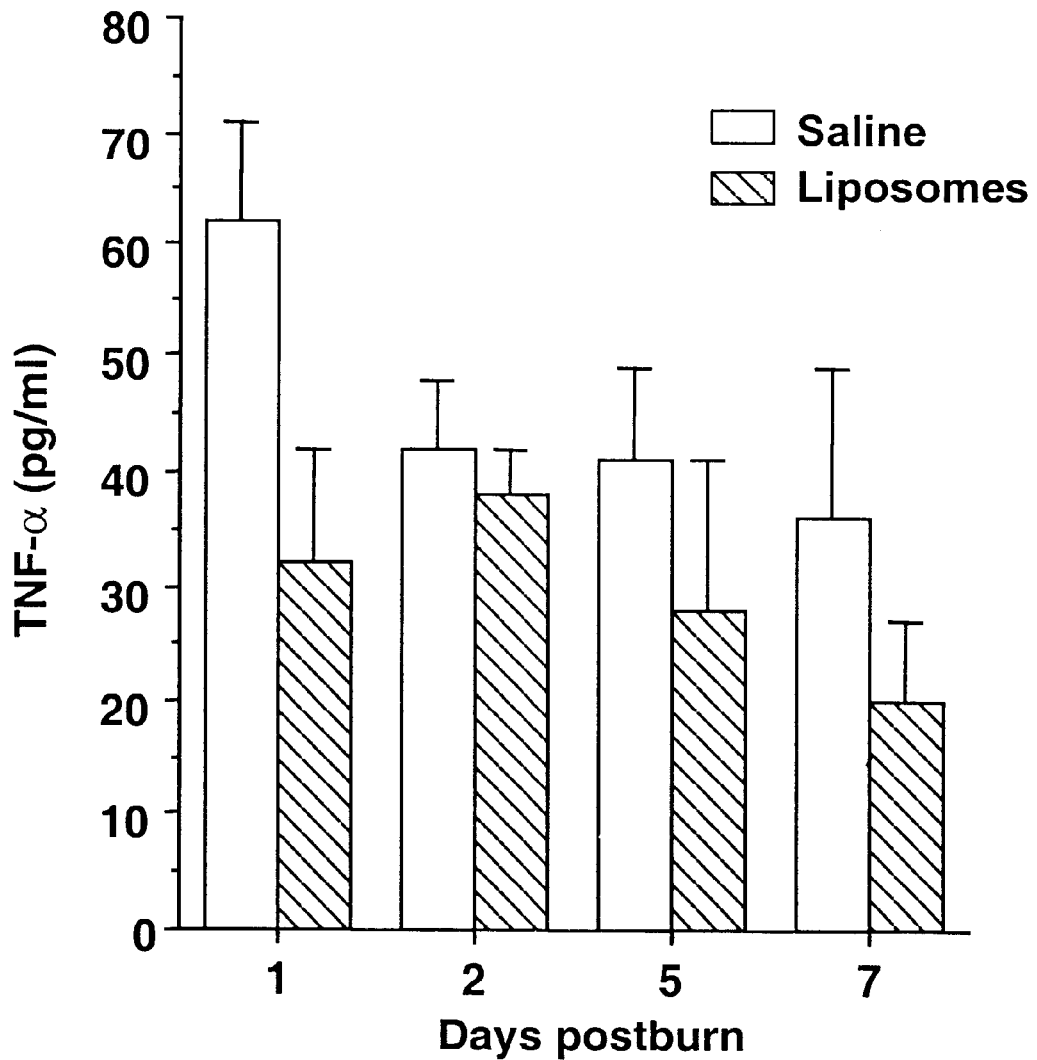
FIG. 8 shows serum TNF-α 1 to 7 days after thermal injury. * Significant difference between saline and liposomes at $p<0.05$. Data presented as means±SEM. (Normal serum TNF-α: 1–10 pg/ml).
Figure 9:
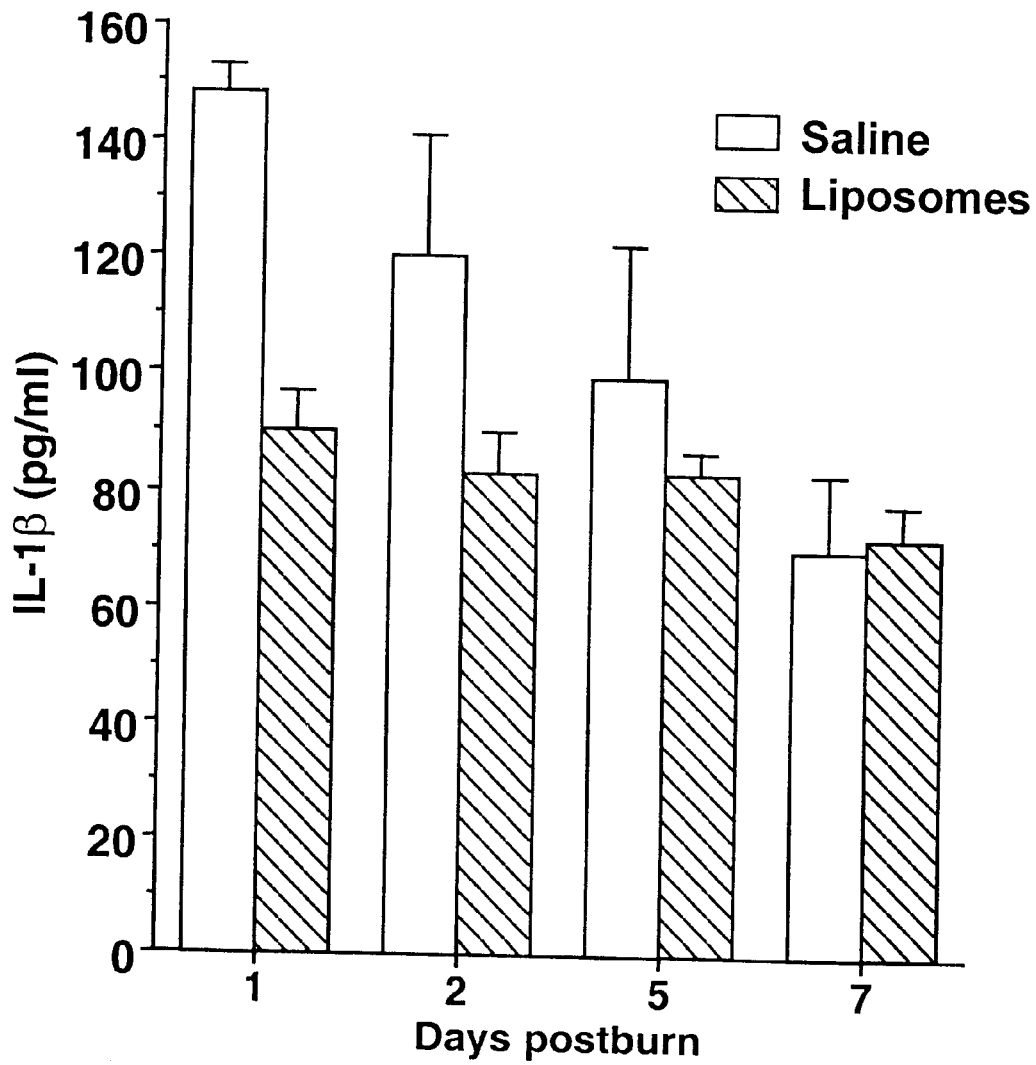
FIG. 9 shows serum IL-1β 1 to 7 days after thermal injury. * Significant difference between saline and liposome administration at $p<0.05$. Data presented as means±SEM. (Normal serum IL-1β: 4–20 pg/ml).

All measured cytokines increased after the thermal injury. Serum IL-1β decreased during the first day postburn and serum TNF-α at 1 and 2 days postburn in rats receiving liposomes compared to controls ($p<0.05$; FIG. 8). No change in serum IL-6 was observed in liposome treated rats compared to controls.

EXAMPLE 8
Biological Efficacy

All rats survived the 60% TBSA scald burn and the drug injections with no deleterious side effects. Wound healing was determined as follows; the wound eschar was left intact for the first 28 days and then removed by gentle traction, with caution taken not to disturb or destroy the healing edge along the periphery. After removing the eschar, the animals were placed on a standard surface and the wound area traced onto acetate sheets along the well-demarcated re-epithelized and non-burned interface and the leading edge of the neoepithelium. The areas of these tracings were calculated by computerized planimetry (Sigma Scan and Sigma Plot software). In addition, skin biopsies were taken from the wound edge at 33 days after burn and light microscopic analysis was performed using established techniques. Histological measurements for linear skin re-epithelization used the HE staining technique.

Figure 10:
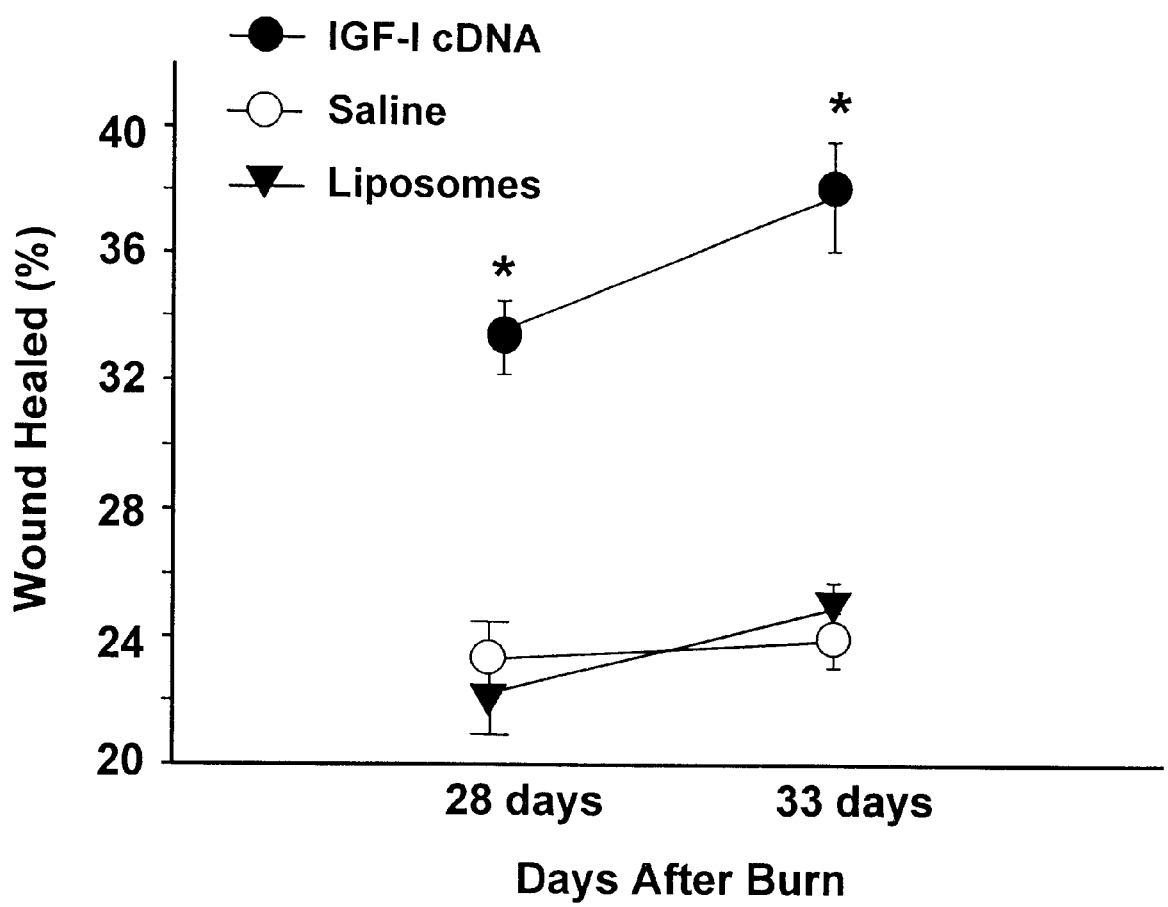
FIG. 10 shows that the area of wound re-epithelization was measured by planimetry. Rats receiving encapsulated IGF-I cDNA constructs had the highest per-cent of re-epithelization throughout the study period compared to the liposomes or saline groups. * Liposome cDNA vs. Liposome and saline (p<0.05). Data presented as mean±SEM.

At 28 and 33 days after the thermal injury, rats receiving the IGF-I cDNA construct showed a significant increase in re-epithelization when compared with those receiving liposomes alone or saline ($p<0.05$; FIG. 10). This enhancement in wound healing is most likely due to a mitogenic stimulus of IGF-I to keratinocytes and fibroblasts, as increased mitogenic activity was found in rats treated with the IGF-I cDNA construct compared with those receiving liposomes alone or saline. Rats receiving the IGF-I cDNA construct had higher total serum protein levels and total liver protein levels compared with rats treated with liposomes or saline ($p<0.05$; Table 5).

TABLE 5

Total protein concentration in serum and liver

| | Saline (n = 10) | Liposomes (n = 10) | IGF-I cDNA (n − 10) |
|---|---|---|---|
| Serum (g/dl) | 5.2 ± 0.1 | 5.3 ± 0.1 | 5.5 ± 0.1* |
| Liver (mg/ml) | 0.60 ± 0.01 | 0.61 ± 0.02 | 0.71 ± 0.03* |

Data presented as mean ± SEM.
*Significant difference vs. Liposomes and saline $p < 0.05$.

EXAMPLE 9
Procurement of Fetal Amnion Membrane Donor Tissue and Preparation of Amnion and Chorion After informed consent, history taking and screening for potential risk factors such as cancer, infectious diseases, drug abuse and sexual behavior, the presumptive donor is tested for Hepatitis B and C, RPR, HIV1, HIV2 (as is routinely done by the SBI skin bank and as defined by AATB). This testing is done at the time of delivery and at a scheduled outpatient appointment 60–90 days after delivery. Immediately after delivery, placentas with adherent fetal membranes are obtained from suitable donors (according to the guidelines of AATB). After preliminary washing with Ringer's solution in the delivery room, the placenta is transferred to a tissue culture medium (e.g., RPMI 1640)

containing antibacterial and antifungal agents and transported at 4° C. to the processing site.

The procurement steps are carried out using aseptic technique such that bacterial and fungal contamination of the product does not occur. Microbiological testing is performed with each processing step so as to monitor contamination. Additional PCR techniques can be performed on the tissue samples to also exclude viral infection (e.g., HIV-1 or -2).

At the processing site (SBI tissue bank facility), additional washing and flushing of the placenta with Ringer's solution via the umbilical vessels is carried out. Amnion and chorion layers are then mechanically separated from each other and from the placenta, and the covering cellular material removed by enzymatic digestion with trypsin (Boehringer Mannheim, Indianapolis, Ind.) (1:1 dilution of distilled water and trypsin for 2 h at 20° C.) followed by repeated rinsing with phosphate buffered saline (according to WO 93/10722). For consistency, prepared amnion is stored using standard control rate freezing techniques. To obtain different tissue properties and characteristics, fetal membrane structures are cross-linked using a 1.5% glutaraldehyde solution (Sigma, St. Louis, Mo.) for 20 min at 20° C., followed by washing in 1.5% glycine (Sigma, St. Louis, Mo.) 3 times for 15 min as described for skin preservation by the Euro Skin Bank (61).

Preparation for definitive storage includes lyophilization using a shelf freeze drying system with a double freeze drying procedure which results in a moisture content of less than or equal to 6% water, or preservation by shaking the fetal membranes in 85% glycerol at 20° C. for two 3 hour periods. The latter allows for a residual moisture of 15% water and assures inactivation of HIV and other viruses (62). The latter treatment results in no remaining viable cells and a diminished antigenicity resulting in decreased immunologic response (63,64). Glycerol-preserved tissue is stored in glycerol at 4° C. Both procedures are completed by transfer of the tissue into a foil bag, allowing for further sterilization by gamma radiation or ethylene gas. Before use, the tissue is reconstituted by immersion in saline/Ringer's solution. Additional wound coverage materials, such as a synthetic fabric comprising type I and II collagens and human skin, are prepared for comparison purposes (U.S. Pat. No. 5,002,071; Walther et al., 1998).

EXAMPLE 10

Cholesterol-containing Cationic Liposomes as a Delivery System for Gene Therapy in Trauma Attenuate the Acute Phase Response in Thermally Injured Rats One major contributor to the hypermetabolism associated with a thermal injury is the increase in acute phase proteins and cytokines [9,10,11]. It was shown herein that administration of cholesterol-containing cationic liposomes improved body weight and the expression of the constitutive hepatic proteins transferrin and total protein after burn compared to saline. It was further shown that liposomes decrease serum type I acute phase proteins and the type I acute phase proteins responsive pro-inflammatory cytokines serum TNF-α and IL-1β. It is likely that the decrease in IL-1β and TNF-α subsequently leads to a decrease in these acute phase proteins.

The reasons for the beneficial effects associated with liposomes are most likely due to the direct effect of the liposomal lipid moieties on damaged cell membranes or to an enhancement of the uptake of extracellular nutrients and the in situ encapsulation and protection of the endogenous growth factors and cytokines elaborated locally as part of the hypermetabolic response which is triggered by acute phase proteins and cytokines. Pro-inflammatory cytokines, in particular TNF-α, inhibit protein synthesis and induce weight loss [16–18]. After a thermal injury, as well as in sepsis, TNF-α serum levels increase along with sepsis-induced muscle proteolysis [19–21]. Decreased serum TNF-α levels are associated with an improvement in net protein balance and a reduction in body weight loss in thermally injured pediatric patients [22,23]. Thus, as shown herein, a decrease in serum TNF-α may preserve body weight and increase serum transferrin levels.

Several studies have attempted to determine the mechanisms by which cationic liposomes exert an inhibitory effect on cytokine expression in vitro, however the exact mechanisms are currently not defined [25–30]. It seems likely that nuclear factor kappa B (NF-κB) plays an important role [27]. NF-κB is a transcription signal and is crucial in the development of the cellular immune and inflammatory response [27]. Due to electrostatic interactions between cells and cationic liposomes, the liposomes bind to the receptor for oxidized low-density lipoproteins (OxLDL) [28,29]. Sambrand and colleagues have shown that this competitive binding and subsequent activation of the OxLDL receptor indirectly suppresses activation and/or binding of NF-κB to its cognate DNA site [28]. Furthermore, Aramaki and colleagues have shown that cationic liposomes inhibit tyrosine phosphorylation of p41, a protein of the MAP kinases transcription factor family, which consecutively leads to a down-regulation of NF-κB [25–27]. The inhibition of p41 and NF-κB inhibits the induction of inducible nitric oxide synthetase (iNOS), which decreases subsequent nitric oxide (NO) expression [25,26]. These changes in the signal pathway have been hypothesized to be responsible for the selective inhibition of TNF-α expression at the post-transcriptional level [25,26,31]. Given that NO and iNOS stimulate IL-1β expression, it seems likely that the inhibition of NO or iNOS activity through cationic liposomes leads to decreased IL-1β expression [32,33]. Therefore, cationic liposome administration apparently proves beneficial in the treatment of inflammatory diseases, in part because of their inhibition of pro-inflammatory cytokine release [31,34].

The administration of cholesterol-containing cationic liposomes modulates the hypermetabolic response by affecting cytokine expression, although the effects of the injection are not likely to persist beyond 5 days. There were no differences in serum cytokine and protein 7 days postburn between liposome-treated and control animals. Furthermore, serum transferrin decreased from day 5 to day 7 postburn in rats receiving liposomes, whereas control-treated animals showed an increase in serum transferrin from day 5 to day 7 postburn. In addition, serum haptoglobin increased from day 5 to 7 in the liposome-treated group, while serum haptoglobin decreased over the same time period in control animals. Therefore, cholesterol-cationic liposomes increased constitutive hepatic proteins and decreased type I acute phase proteins, with associated decreases in IL-1β and TNF-α levels. Thus, cholesterol-cationic liposomes appear to be suitable as a delivery system for gene therapy in trauma, because liposomes favorably modulate the trauma-induced hypermetabolic response and do not display the cytotoxicity typically associated with the use of other cationic liposomes in vivo [4,7].

EXAMPLE 11

Figure 11:
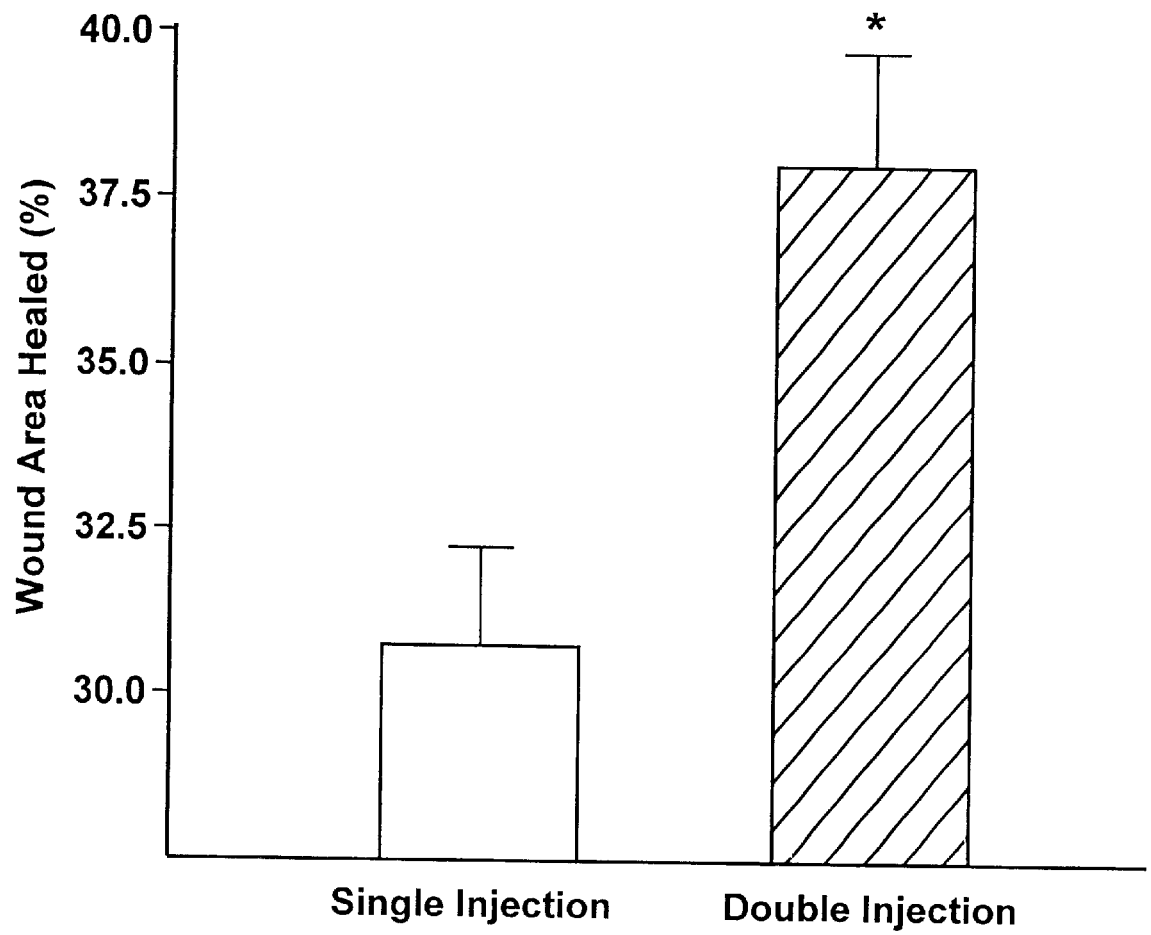
FIG. 11 shows the area of wound re-epithelization that was measured by planimetry. Rats receiving multiple injections of encapsulated IGF-I cDNA constructs had the highest percent of re-epithelization throughout the study period compared to single injections. * IGF-I cDNA multiple injections vs. single injections, p<0.05. Data presented as means±SEM.

Clinical Impact of Multiple Injections of an IGF-I Gene Construct After Thermal Injury All rats in each group survived the 60% TBSA scald burn and drug injections with no evidence of any deleterious side effects. Total body weight increased at nearly 2% per week for the first 4 weeks postburn in animals transfected with single and multiple injections of liposomes-IGF-I cDNA construct, with no differences between the two groups. Rats receiving multiple injections of the IGF-I cDNA construct had higher serum protein levels (single injection 5.2±0.05 g/dl vs. multiple injection 5.5±0.06 g/dl) and total liver protein (single injection 0.64±0.002 mg/ml vs. multiple injection 0.71±0.03 mg/dl) compared to a single injection (p<0.05). After the eschar was removed, the per cent area of burn wound re-epithelization was significantly larger 33 days after burn in rats receiving the double injection of IGF-I cDNA compared to the single injection (38±2% vs. 31±2% respectively; p<0.05). These results were confirmed by histological measurements of linear re-epithelization. Rats treated with double injections of IGF-I cDNA showed significantly more re-epithelization when compared to single injections (p<0.05; FIG. 11).

Figure 12A:
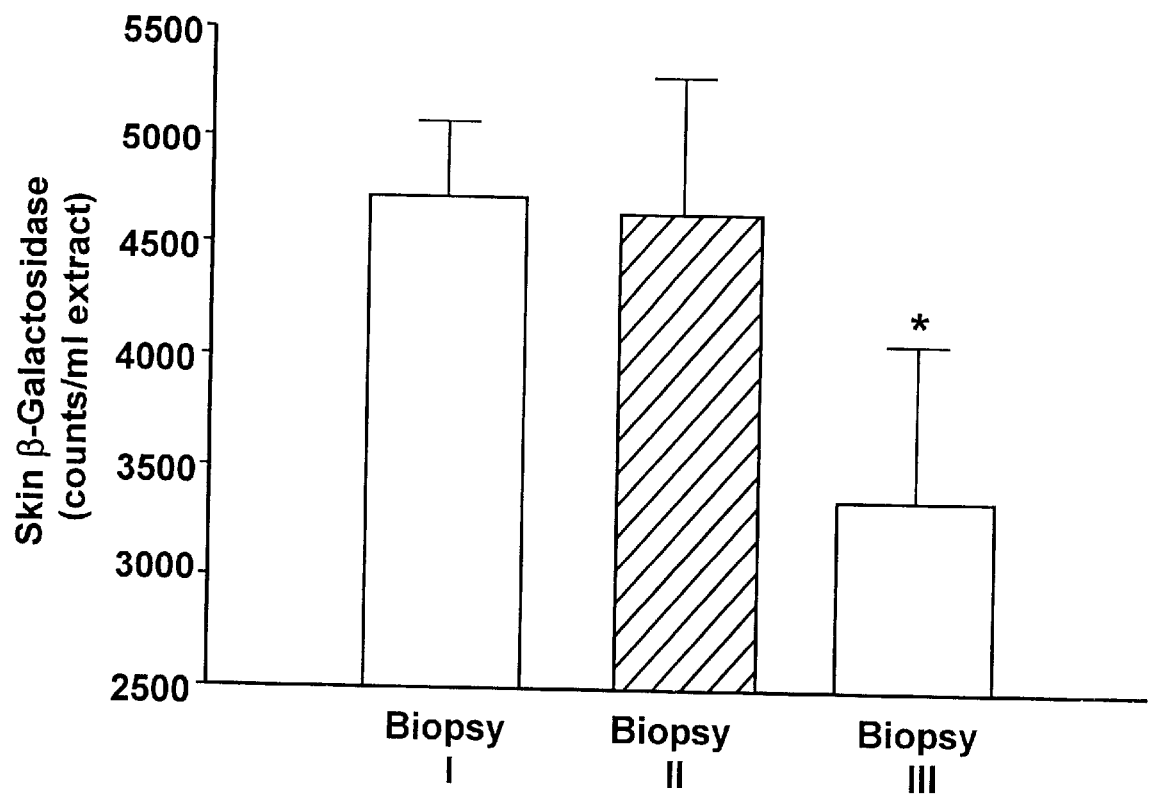
FIGS. 12A and 12B show that the presence of β-galactosidase protein was detected by chemiluminescent reporter gene assay in skin biopsies I, II and III. (12A) Rats receiving single injection of the cDNA construct demonstrated a significant decrease in β-galactosidase expression along the wound edge. * Significant difference between skin biopsy I vs. III, p<0.05. (12B) Rats receiving multiple injections demonstrated consistent elevated levels of β-galactosidase expression. There was no differences between skin biopsy I, II or III. Data presented as means±SEM.
Figure 12B:
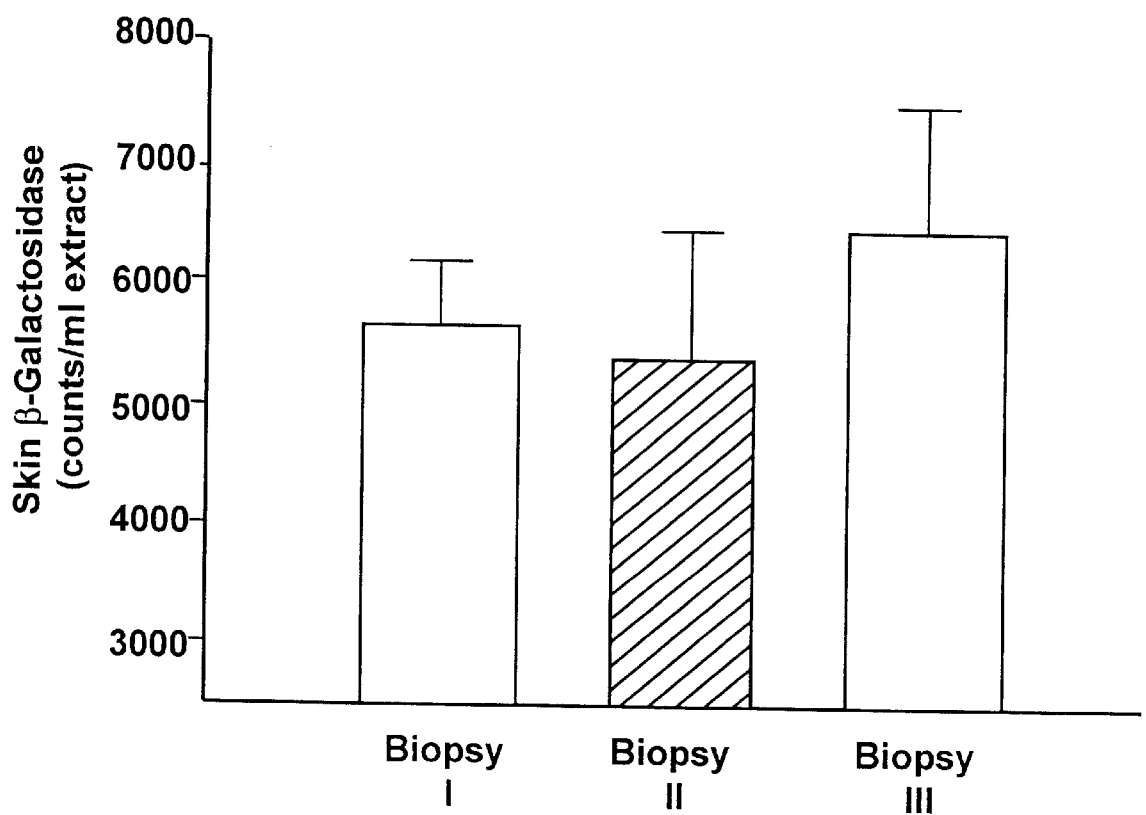
Figure 13A:
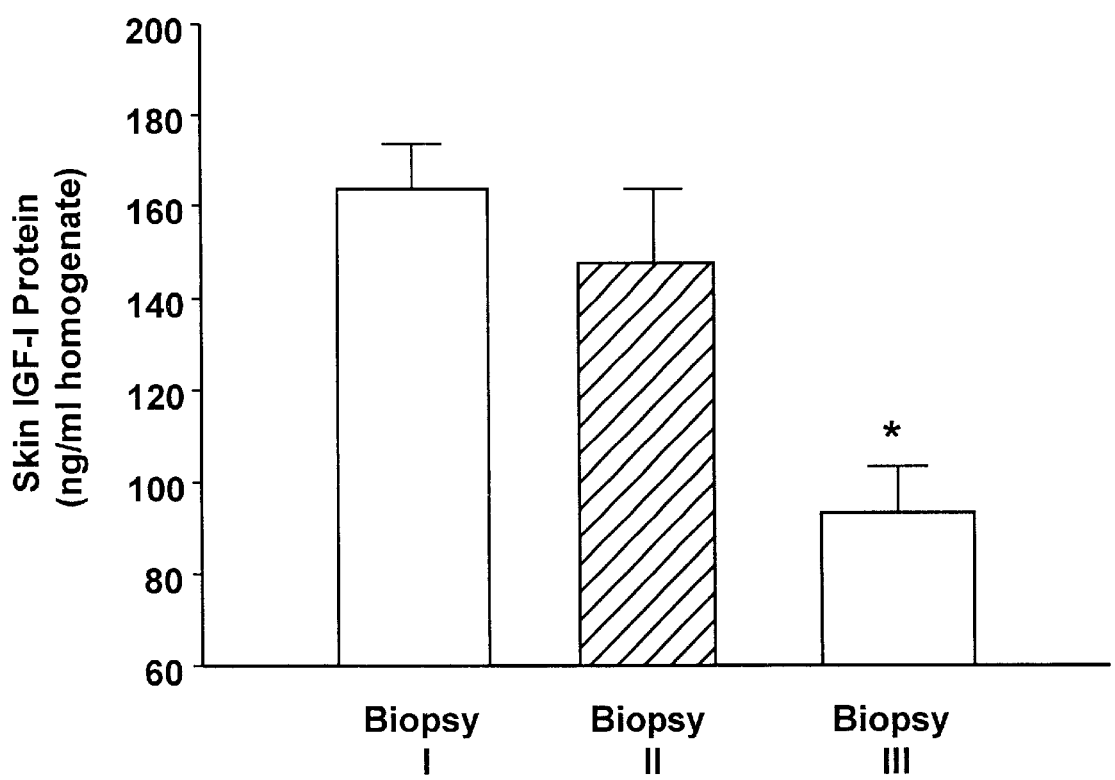
FIGS. 13A and 13B show the IGF-I protein concentration in skin biopsies I, II and III that was measured by RIA. (13A) Rats receiving a single injection demonstrated a decrease in IGF-I concentration from biopsy I to III. * Significant difference between skin biopsy I vs. III, p<0.05. (13B) Animals receiving multiple injections demonstrated consistent high levels of IGF-I. Data presented a s means±SEM.
Figure 13B:
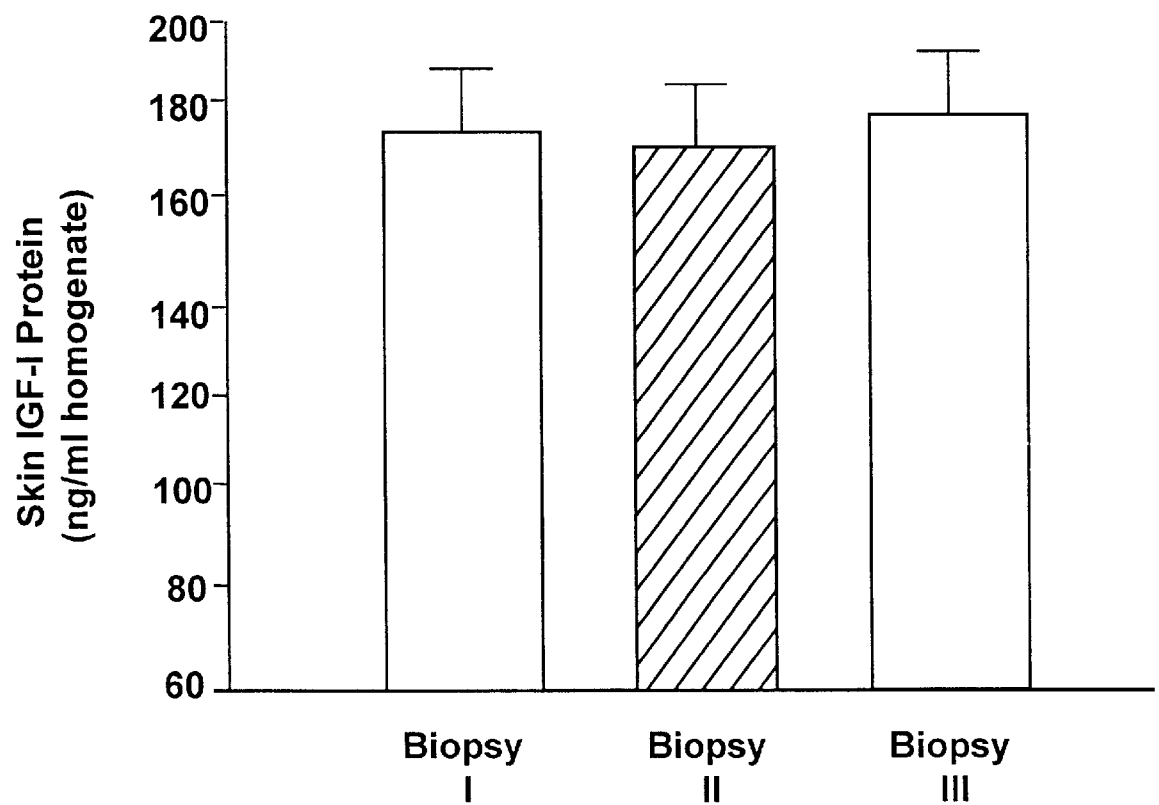

Transfection, determined by chemiluminescent reporter gene assay to detect β-galactosidase, was increased around the wound perimeter in animals receiving multiple injections of liposome encapsulated Lac Z cDNA and IGF-I cDNA constructs when compared to single injections (p<0.05; FIG. 12A, B). Skin concentrations of IGF-I protein decreased from the skin biopsy point I to the skin biopsy point III in rats receiving the single injection of IGF-I cDNA construct along the wound edge (FIG. 13A). Animals receiving double injections of the cDNA construct showed consistent elevated IGF-I protein concentrations along the entire wound edge (FIG. 13B). Additionally, transfection was detectable as early as one day after subcutaneous injection of the LacZ gene. The rate of transfection increased and peaked 5 days after injection. In contrast to in vitro experiments in which transfection was not detectable 7 days after administration, transfection of skin cells was still detectable 7 and 14 days after in vivo injection.

After the subcutaneous injection of the IGF-I cDNA and the reporter Lac Z construct, transfected dermal cells, myofibroblasts, endothelial cells, and macrophages were identified, including multinucleate giant cells known to be proliferative. mRNA levels for IGF-I were increased in the skin of rats transfected with the IGF-I construct. That the mRNA was translated into protein is consistent with the observed increase in skin IGF-I protein concentrations. This transient increase in the local expression of IGF-I protein could cause a concurrent stimulation of IGFBP-3 protein synthesis and increased levels of the biologically active complex IGF-I/IGFBP-3 locally without any concomitant supraphysiological increases in circulating levels of free IGF-I protein, and therefore, no deleterious side effects [49,50]. The small amounts of IGF-I protein expressed after liposomal transfections are effective in a paracrine fashion without the adverse effects of larger dosages required by systemic administration.

An elevation of IGF-I protein concentration in the skin improved wound healing in terms of re-epithelization and dermal cell recovery along with dermal cell mitosis. Rats receiving the IGF-I cDNA also had increased body weight and total protein concentrations in serum and liver. As neither transfection nor increased IGF-I expression was observed in blood, liver, spleen or kidney, the beneficial effects (e.g., preserved body weight, increased serum and liver protein concentration) are due to enhanced wound healing and improved dermal cell recovery after injury and result from the paracrine effects associated with higher local levels of IGF-I protein as opposed to changes in circulating levels of IGF-I protein resulting from systemic transfection. IGF-I exerted mitogenic effects on keratinocytes and fibroblasts with the stimulation of collagen synthesis, as well as improved cell recovery after injury, leading to enhanced wound healing [40,41,48].

The advantages of early wound closure, demonstrated in several clinical studies [36,37], include a diminished hypermetabolic burn response and a decrease in inflammatory mediators, such as IL 1, IL-6, IL-8, and TNFα [36,37]. Furthermore, IGF-I protein decreases pro-inflammatory cytokines IL-1β and TNF-α expression after thermal injury [57]. Therefore, IGF-I may exert its systemic beneficial effect through the enhancement of re-epithelization and/or the decrease of the pro-inflammatory response in the skin, which is one of the major sources of cytokine synthesis and release after burn [58,59].

It is demonstrated herein that transfection is restricted to the skin within a small perimeter of the sites of injection. The nature of the expression of IGF-I was most likely due to interactions between the positive surface charges on cationic liposomes and negatively charged outer cell membranes, which restricted liposomal migration [54]. However, transfection and IGF-I expression was significantly increased when multiple injection sites were used when compared to a single injection site. Multiple injections of IGF-I cDNA demonstrated a consistent elevation of IGF-I protein expression along with improved wound healing, whereas a single injection demonstrated less IGF-I protein along the wound. This finding is clinically relevant, because the liposomes encapsulating the gene should be applied at well-defined distances from trauma sites to provide optimal transfection and protein expression.

Experiments herein demonstrate that the subcutaneous administration of liposome-encapsulated IGF-I cDNA constructs successfully transfected dermal cells. It is also demonstrated that the cDNA was transcribed into mRNA and translated into IGF-I protein. Multiple injections of the IGF-I cDNA increased the number of transfected cells, and protein expression, which improved wound healing when compared to a single injection. The process of transfection, transcription and translation was restricted to the skin, as systemic transfection or increased systemic IGF-I protein expression was not observed. The biological responses to increased skin IGF-I were an enhancement in wound healing with subsequent systemic improvements to the hypermetabolic response.

EXAMPLE 12

Liposome-encapsulated IGF-I cDNA Gene Transfer Increases IGF-I Protein in Skin Cells to Promote Wound Healing The use of transient gene therapy after trauma is a new approach to improve clinical outcome and mortality. Of major importance is the selection of the appropriate vector for gene delivery [1,2]. Non-viral composition, non-cytotoxicity, increased infectivity and anti-inflammatory activity make cholesterol-containing cationic liposomes a promising approach to ameliorate the burn-induced hypermetabolic response [4,51–53]. It has been shown herein that cholesterol-containing cationic liposomes are an effective delivery system in vivo after thermal injury. Additionally, the mechanisms by which DNA transfection and subsequent induced gene expression alter thermal trauma responses are reported herein, as well as the effects of IGF-I gene transfer in a model of thermal injury. It was shown herein that the subcutaneous administration of liposome-encapsulated IGF-I cDNA constructs successfully transfected dermal cells and that the cDNA was transcribed into mRNA and translated into IGF-I protein. The process of transfection, transcription and translation was restricted to the skin. The biological responses to increased skin IGF-I were an enhancement in wound healing with subsequent systemic improvements to the hypermetabolic response. From these findings, it is concluded that cholesterol-containing cationic liposomes encapsulating an expression plasmid vector for IGF-I cDNA, when given to rats with a 60% TBSA thermal injury, are effective in increasing IGF-I skin protein concentrations and thereby enhancing wound healing.

EXAMPLE 13
Comparison of Membranes for Cover Material

To determine the biological efficacy of the different wound coverage materials, outcome measurements are taken weekly over a time period of 4 months and include: a) wound healing time; b) re-epithelization by computerized planimetry, histological/electron microscopic measurements; c) integrity by take rate and histology and immune markers of rejection; and d) elastic rates and contraction. Based on this data, the functionality and the efficacy of the different cover materials are evaluated and the most suitable determined.

Furthermore, gene transfer is measured by: a) histochemical and chemiluminescent assays of reporter gene ($\beta$-galactosidase) expression as a screen for transfection; b) northern blot analysis for IGF-I mRNA in the skin as a marker for transcription; and c) radioimmunoassays to detect the IGF-I protein in the skin.

Additionally, the acute phase response is determined by: a) body weight, nutritional intake, nitrogen balance and protein concentration in muscle and liver; b) constitutive hepatic protein production (albumin, transferrin, pre-albumin and retinol-binding protein) determined by nephelometer; c) acute phase proteins (haptoglobin, $\alpha$1-acid-glycoprotein, $\alpha$2-macroglobulin and fibrinogen) determined by enzyme-linked immunoassays (ELISA) and nephelometer; and e) cytokines (interleukin-1$\beta$, interleukin-4, interleukin-6, interleukin-8, interleukin-10, tumor-necrosis factor-$\alpha$ and interferon-$\gamma$) determined by ELISA.

EXAMPLE 14
Wound Coverage of a Burn Injury

To more accurately simulate clinical treatment, each of the 15 Yorkshire swines receive a 35% total body surface area (TBSA) full-thickness flame burn (standard model) under anesthesia and analgesia. The animals remain restrained in a hammock for 24 hours and receive intensive care, including adequate resuscitation and analgesia. To mimic clinical setting, twenty-four hours after receiving the burn, the animals undergo wound excision and grafting. This is approximately the same time frame after thermal injury that human patients are excised and grafted. Under general anesthesia and analgesia, the entire burn wound is excised and immediately covered with either human amnion or human amnion impregnated with liposomal gene complexes. Only one type of cover material is used per animal, as opposed to different types of wound coverage material on the dorsum of the same animal. The cover is stapled to the unburned wound and covered with gauze containing triple-antibiotic ointment and a bulky pressure dressing. Staples and/or sutures are used as required. Following surgery, the study animals were suspended in a hammock restraint while recovering from anesthesia as described above.

These experiments determine the effect of different cover materials with and without the liposomal expression vectors on the hepatic acute phase response and correlates those effects to wound healing. Therefore, immediately after burn, surgery, and at post-operative days 2, 4, 6, 8, 10, 12, 14 and 16, venous blood is drawn from the animal and examined for constitutive hepatic proteins, acute phase proteins and cytokines. The human amnion or INTEGRA™ represents a reservoir for liposomal gene constructs. Due to electrostatic interactions between the cell/wound surface, liposomes will migrate out of the impregnated cover material and transfect skin and wounded cells to thereby increase local IGF-I concentration. The increase in IGF-I concentration subsequently improves wound healing.

EXAMPLE 15
Additional Growth Factors in Concert with IGF-I

The combination of fetal membrane or human cadaver skin impregnated with liposomal gene constructs accelerate and improve the graft take, functionality, wound healing and the hypermetabolic response after injury. The liposomal gene construct(s) may encode the insulin-like growth factor-I (IGF-I), keratinocyte growth factor (KGF), growth hormone (GH), fibroblast growth factor (FGF), epidermal growth factor (EGF), platelet derived growth factor (PDGF), transforming growth factor-$\beta$ (TGF-$\beta$), or any combination of the above-mentioned factors.

Conclusion

Liposomes containing a cDNA encoding IGF-I have been shown to preserve body weight after a 60% TBSA wound, prevent muscle protein wasting, improve wound healing and increase IGF-I protein concentration in the skin. Furthermore, cell transfection and subsequent IGF-I gene expression is a local event restricted to the injection site. As no significant differences were detected in serum IGF-I and IGFBP-3 concentrations, the beneficial effects of the liposome gene delivery are due to localized enhanced wound healing, rather than systemic changes in circulating IGF-I.

The present invention demonstrates that cDNAs encoding growth-enhancing agents favorably modulates the hyper-metabolic response after thermal injury, and that liposome constructs can be used effectively as a delivery system for gene transfections. The therapeutic benefits of liposomal gene transfection was further enhanced by increasing the number of injection sites around the wound edges or by "wound dressing", which increased the number of transfected cells and the concomitant levels of gene expression. Therefore, fetal membrane, or other wound coverage materials, impregnated with liposomes containing the IGF-I gene construct improves wound healing and represents the optimal burn wound treatment. This application of liposomal gene therapy is used to impregnate human cadaver skin, amnion or other types of wound coverage and/or closure materials and may revolutionize plastic, reconstructive, trauma and burn surgery and improve the clinical outcome of those patients.

The following references were cited herein:

1. Firedmann T. Scientific American. 1997. 6: 96–101.
2. Felgner P L. Scientific American. 1997. 6: 102–106.
3. Felgner, P. L., et al. Annals of the New York Academy of Sciences. 1995. 772: 126–139.
4. Felgner, P. L. Human Gene Therapy. 1996. 7: 1791–1793.
5. Wheeler, C. J., et al. Proc Natl Acad Sciec 1996. 93 (21): 11454–11459.
6. Sharata, et al. Intern J Dermatalogy. 1996. 35(11): 761–769.
7. Fey G, & Gauldie J. The acute phase response of the liver in inflammation. In Popper, H., Schaffner, F. (Eds.). Progress in Liver Disease. Philadelphia: W. B. Saunders, 1990. 89–116.
8. Rotheschild M A, et al. Hepatology. 1988. 8:385–401.

9. Moshage H. J Pathol. 1997. 181: 257–266.
10. Selzman C H, et al. Shock 1998; 10: 309–318.
11. Gilpin D A, et al. Surgery. 1996. 119 (6): 664–673.
12. Jarrar D, et al. Arch. Surg 1997. 132: 1171–1176.
13. Xia Z F, et al. Surgery. 1996. 119: 664–673.
15. Herndon D N, et al. J. Surg. Res. 1978. 25: 394–403.
16. Beutler B, & Cerami A. Adv Immunol. 1988. 42: 213–231.
17. Moldawer L L, et al. Ann Rev Nutr. 1988. 8:585–609.
18. Frost R A, et al. Endo. 1997. 138 (10): 4153–4159.
19. Marano M, et al. Am Burn Assoc Ann Proc. 1988. 20: 18.
20. Yamada Y, et al. Burns. 1996. 22 (8): 587–593.
21. Balteskard L, et al. Scand J Infect Dis. 1997. 29: 393–399.
22. Gore D C, et al. Arch Surg. 1991. 126: 38–43.
23. Chrysopoulo M T, et al. Arch Surg. 1998. (in press).
24. Pennanen N, et al. Pharm Res. 1995. 12: 916–922.
25. Aramaki Y, et al. Biochem Biophys Res Com. 1996. 220: 1–6.
26. Aramaki Y, et al. Biochem Biophys Res Com. 1997. 231: 827–830.
27. Mulsch A, et al. Biochem Biophys Res Com. 1993. 191: 1301–1308.
28. Sambrand et al. Proc Natl Acad Sci USA. 1995. 92: 1396–1400.
29. Shackelford R E, et al. J Biol Chem. 1995. 270: 3745–3478.
30. Mulsch A, et al. FEBS Lett. 1993. 321: 215–218.
31. Brisseau G F, et al. Antimicrobial Agents and Chemotherapy. 1994. 38: 2671–2675.
32. Xiao B G, et al. Neurosci Lett. 1998. 249: 17–20.
33. Arnush M, et al. J Clin Invest. 1998. 102: 516–526.
34. Pierre, E., et al. 1996. Growth hormone therapy in the treatment of burns. In: M. H. Torosian, ed. Growth hormone in critical illness: research and clinical studies. R. G. Landes Co, Texas. Pp 105–116.
35. Meyer, N. A., et al. 1996. J Trauma 31 (6): 1008–1012.
36. Herndon, D. N., et al. 1989. Ann. Surg. 209 (5): 547–553.
37. Rodriguez, J. L., et al. 1993. J. Trauma 34: 684–694.
38. Zaizen, Y., et al. 1990. J Ped Surg (25): 70.
39. Herndon, D. N., et al. 1990. Ann. Surg. 212: 424.
40. Martin, P. 1997. Science 276: 75–81. 1997.
41. Steenfos, H. 1994. Scand J Plast Reconstr Hand Surg 28: 95–105.
42. Huang, K. F., et al. 1993. Arch Surg 128: 47–54.
43. Strock, L. L., et al. 1990. Surgery 108 (2): 161–164.
44. Clemmons, D. R. 1994. Ann Intern Med 120: 596–597.
45. Lo, H. C., et al. 1995. Am J Physiol 269: E368–E376.
46. Guler, et al. 1988. Proc Natl Acad Sci USA 85: 4889–4893.
47. Walker, J. L., et al. 1991. N Engl J Med 324: 1483–1488.
48. Pierre, et al. 1997. J Burn Care Rehab 18 (4): 287–291.
49. Jabri, N., et al. 1994. Diabetes 43: 369–374.
50. Bondy, C. A., et al. 1994. Ann Int Med 120: 593–601.
51. Filion, & Philips, Br J Pharmacol 122: 551–557. 1997.
52. Noguchi A, et al. FEBS Lett; 433: 169–173. 1998.
53. Caplen N J, et al. Nat Med; 1: 39–46. 1995.
54. Alexander, & Akhurst. 1995. Human Molecular Genetics 4 (12): 2279–2285.
55. O'Connor, & Culp. Biotechniques; 17: 502–509. 1994.
56. Lasic D D. Liposomes in gene delivery. CRC Press, New York.
57. IGF-I APR
58. Kupper T S, et al. Surgery 100: 409–414. 1986.
59. Garner W L, et al. Surgery; 116: 42–48. 1994.
60. Herndon, D N, et al. 1978. J. Surg. Res.; 25:394–403.
61. Hoekstra M J et al., 1994. *Burns* 20:S43–47.
62. van Baare J et al., 1994. *Burns* 20:S77–80.
63. Hettich R et al., 1994. *Burns* 20:S71–76.
64. Richters C D et al., 1997. *J. Burn Care Rehabil.* 18:228–233.
65. U.S. Pat. No. 4,361,552; Baur, Jr.
66. U.S. Pat. No. 5,002,071; Harrell Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An enhanced wound dressing for external wounds, comprising:
    a wound coverage material; and
    a cholesterol-containing cationic liposome, said liposome comprising at least one gene encoding insulin-like growth factor-I (IGF-I) wherein the concentration of said gene(s) in said liposomes is about 2.2 $\mu$g/10 $\mu$l liposomes.

2. The enhanced wound dressing of claim 1, wherein said wound coverage material is selected from the group consisting of human fetal amnion, human fetal chorion, human cadaver skin, and synthetic skin.

3. A composition for enhancing wound healing of external wounds, comprising:
    a cholesterol-containing cationic liposome, said liposome comprising at least one gene encoding insulin-like growth factor-I (IGF-I) wherein the concentration of said gene(s) in said liposomes is about 2.2 $\mu$g/10 $\mu$l liposomes; and
    a pharmaceutically acceptable carrier.

4. The composition of claim 3, wherein said wound is selected from the group consisting of thermal trauma, chemical trauma, excisional trauma, surgical trauma and abrasion.

5. The composition of claim 3, wherein said composition is packaged such that said composition can be loaded into a syringe.

6. The composition of claim 3, wherein said composition is packaged in a syringe.

* * * * *

UNITED STATES PATENT AND TRADEMARK OFFICE
CERTIFICATE OF CORRECTION

PATENT NO. : 6,576,618 B1
DATED : June 10, 2003
INVENTOR(S) : David N. Herndon, Jose R. Perez-Polo and Robert E. Barrow It is certified that error appears in the above-identified patent and that said Letters Patent is hereby corrected as shown below:

Column 1,
Line 36, please replace the comma after "(donor site)" with a semicolon.

Column 2,
Line 23, please insert the word -- properties -- after "noninflammatory".

Column 4,
Line 67, "per-cent" should read -- percent --.

Column 6,
Lines 56-60, please replace all the brackets with parentheses.

Column 7,
Line 14, please delete the semicolon after "in vivo".

Column 9,
Lines 32-33, please put "Remington's Pharmaceutical Science" in quotation marks.
Line 33, please place parentheses around "17$^{th}$ Ed. (1990)".
Lines 34-35, "Goodman and Gilman's: The Pharmacological Basis of Therapeutics" should not be italicized.
Lines 34-35, please put "Goodman and Gilman's: The Pharmacological Basis of Therapeutics" in quotation marks.
Line 35, please place parentheses around "8$^{th}$ Ed. (1990)".

Column 12,
Line 1, please delete "USA".

Column 13,
Line 11, please delete "USA".

Column 14,
Line 50, in the footnote for Table 5, "Liposomes" should read -- liposomes --.

Column 15,
Line 25, "(61)" should read -- [61] --.
Line 30, "3 hour" should be hyphenated.
Line 32, "(62)" should read -- [62] --.
Line 35, "(63, 64)" should read -- [63, 64] --.

Column 17,
Line 22, "FIG." should read -- FIGS. --.

UNITED STATES PATENT AND TRADEMARK OFFICE
CERTIFICATE OF CORRECTION

PATENT NO.   : 6,576,618 B1
DATED        : June 10, 2003
INVENTOR(S)  : David N. Herndon, Jose R. Perez-Polo and Robert E. Barrow It is certified that error appears in the above-identified patent and that said Letters Patent is hereby corrected as shown below:

Column 19,
Line 47, "twenty-four" should read -- 24 --.

Column 20,
Line 53, please insert a period after "Felgner P".
Line 58, "Sciec" should read -- Sci. --.
Line 62, please replace the comma after "Fey G" with a period.
Line 67, please insert a comma after "Rotheschild".
Line 67, please insert periods after "M" and "A".

Column 21,
Line 7, please delete the comma after "Beutler B".
Line 36, please delete the comma after "Pierre".

Column 22,
Line 3, please delete the semicolon after "Biotechniques".
Line 4, please move "1994" to after "Biotechniques".
Line 7, please insert a period after "APR".
Line 8, please move "1986" to before "Surgery".
Line 9, please move "1994" to before "Surgery".
Line 10, please delete the periods after "J" and "Surg".
Line 10, please delete the semicolon after "Res.".
Lines 11, 12, 13 and 14, please delete the comma after "et al.".
Lines 11, 12 and 13, "Burns" should not be italicized.
Line 14, "J Burn Care Rehabil" should not be italicized.
Line 17, please insert a period after "Harrell".

Signed and Sealed this

Third Day of February, 2004

JON W. DUDAS
*Acting Director of the United States Patent and Trademark Office*